(12) United States Patent
Kim et al.

(10) Patent No.: US 9,057,715 B2
(45) Date of Patent: Jun. 16, 2015

(54) CELL CULTURE APPARATUS AND MASS AUTOMATIC CELL CULTURE DEVICE HAVING IT

(75) Inventors: Kyung Suk Kim, Seoul (KR); Jai Jun Choung, Seoul (KR)

(73) Assignee: CORESTEM CO., LTD., Cheongwon-gun, Chungcheongbuk-do (KR)

( * ) Notice: Subject to any disclaimer, the term of this patent is extended or adjusted under 35 U.S.C. 154(b) by 1233 days.

(21) Appl. No.: 12/745,029

(22) PCT Filed: Nov. 28, 2008

(86) PCT No.: PCT/KR2008/007037
§ 371 (c)(1),
(2), (4) Date: May 27, 2010

(87) PCT Pub. No.: WO2009/069962
PCT Pub. Date: Jun. 4, 2009

(65) Prior Publication Data
US 2010/0304472 A1    Dec. 2, 2010

(30) Foreign Application Priority Data

Nov. 30, 2007    (KR) ........................ 10-2007-0123914

(51) Int. Cl.
*C12M 1/24*    (2006.01)
*C12M 3/00*    (2006.01)
(Continued)

(52) U.S. Cl.
CPC ........... *G01N 35/1095* (2013.01); *C12M 23/08* (2013.01); *C12M 23/22* (2013.01);
(Continued)

(58) Field of Classification Search
CPC ...... C12M 23/08; C12M 23/22; C12M 23/38; C12M 23/44; C12M 27/10; C12M 29/00; C12M 41/48; G01N 35/1095
USPC .......... 435/173.8, 287.6, 293.1, 289.1, 297.1, 435/304.1, 304.2, 304.3, 297.2, 297.5, 435/303.1, 305.1, 307.1; 604/154
See application file for complete search history.

(56) References Cited

U.S. PATENT DOCUMENTS 4,307,193 A    12/1981    Iizuka
4,335,215 A *  6/1982    Tolbert et al. ................. 435/403
(Continued)

FOREIGN PATENT DOCUMENTS

JP    2005-095015    4/2005
JP    2007-185165    7/2007
(Continued)

OTHER PUBLICATIONS

International Search Report from International Application No. PCT/KR2008/007037, dated Jun. 19, 2009.

*Primary Examiner* — Michael Marcheschi
*Assistant Examiner* — Shanta G Doe
(74) *Attorney, Agent, or Firm* — Clark & Elbing LLP

(57) ABSTRACT

The present invention relates to a cell culture apparatus and a mass automatic cell culture device having it. There is provided a cell culture apparatus comprising a cylindrical cell culture flask which is air-tightly sealed and formed of a transparent material to observe an internal portion thereof, an injection unit for supplying the cell and the culture solution into the cell culture flask, a collection unit for discharging the cells and the culture solution from the cell culture flask, and a cell culture flask receiving part which is comprised of first and second vertical frames in which a plurality of injecting parts and collecting parts, and plate type connection parts which are respectively disposed between upper ends and lower ends of the two opposed vertical frames to be spaced apart from each other in regular intervals, and a mass automatic cell culture device having it.

5 Claims, 20 Drawing Sheets

(51) Int. Cl.
  *G01N 35/10* (2006.01)
  *C12M 1/00* (2006.01)
  *C12M 3/04* (2006.01)
  *C12M 1/36* (2006.01)

(52) U.S. Cl.
  CPC .............. *C12M 23/38* (2013.01); *C12M 23/44* (2013.01); *C12M 27/10* (2013.01); *C12M 29/00* (2013.01); *C12M 41/48* (2013.01)

(56) References Cited

U.S. PATENT DOCUMENTS

| | | | | |
|---|---|---|---|---|
| 4,639,422 | A * | 1/1987 | Geimer et al. | 435/297.3 |
| 5,350,080 | A * | 9/1994 | Brown et al. | 220/62.21 |
| 6,197,574 | B1 * | 3/2001 | Miyamoto et al. | 435/287.6 |
| 6,596,081 | B1 * | 7/2003 | Arnowitz et al. | 117/201 |
| 7,682,823 | B1 * | 3/2010 | Runyon | 435/305.2 |
| 2002/0045861 | A1 * | 4/2002 | Tribe | 604/154 |
| 2006/0128005 | A1 * | 6/2006 | Hasegawa et al. | 435/286.2 |
| 2006/0223155 | A1 * | 10/2006 | Streeter | 435/173.8 |
| 2007/0148764 | A1 * | 6/2007 | Suzuki et al. | 435/293.1 |
| 2008/0274541 | A1 * | 11/2008 | Selker et al. | 435/289.1 |

FOREIGN PATENT DOCUMENTS

| | | | |
|---|---|---|---|
| KR | 10-2002-0065128 A | | 8/2002 |
| WO | WO/2005/059091 | * | 5/2005 |

\* cited by examiner

CELL CULTURE APPARATUS AND MASS AUTOMATIC CELL CULTURE DEVICE HAVING IT

CROSS-REFERENCE TO RELATED APPLICATIONS

This application is the U.S. national stage filing under 35 U.S.C. §371 of international application PCT/KR2008/007037, filed Nov. 28, 2008, which claims benefit of Korean Patent Application 10-2007-0123914, filed Nov. 30, 2007.

BACKGROUND OF THE INVENTION

1. Field of the Invention

The present invention relates to a cell culture apparatus for culturing a cell using a culture solution and various gases, particularly to a cell culture apparatus in which a cell growth process is observed and cells is mass-produced and easily cultured without much time and effort by using an automatic system, and a mass automatic cell culture device having it.

2. Background of Technique

Cell culture comprises aseptically cutting off tissue sections from multicellular organisms and providing nutritive components to them, followed by incubation for cell proliferation in a vessel. The tissues of plants can be immortally proliferated.

A cell culture method includes a coverglass method, a flask method, a rotating tube method and the like. Generally, endosperm, leukocyte or spleen extracts are used to promote the growth of cultured tissues while its essential materials are not clearly elucidated yet. Recently, an antibiotic or an eagle culture solution containing vitamins and amino acids are often used.

The tissue culture permits a single cell to culture to a cell population, a small organ or a plant tissue.

The culture of living cells in a test tube is performed for various purposes, for example, recovery of additional by-products generated by cellular metabolisms, preparation of virus vaccines, culture of cells to fabricate an artificial organ, production of medicines by manipulating genes of an animal cell, breeding of a plant by cell fusion.

In general, the culture of animal cells requires culture media containing nutrients such as amino acids, sugars, inorganic nutrients and vitamins, and their culture conditions are complicated. The plant cells have high viability due to their photosynthesis capabilities compared with animal cells, and thus it is easy to culture them but their proliferation rate is slow.

In the field of biotechnology which has been rapidly developed since the 1980s, the importance of the culture technology for mass-producing animal cells has been emerged as animal cell culture technology has played an important role in industrialization of biotechnology drugs.

The animal cells derived from the tissues of animals or human can be cultured by floating them in a culture medium or attaching them to a substrate. The blood-derived cells (e.g., hematopoietic stem cells) are primarily involved in suspension cells and adherent cells include the cells from the tissues such as skin, liver or lung, embryonic stem cells or mesenchyma stem cells.

The suspension cells per se enable to grow under a suspended condition in the medium while cell adhesion on the surface of solid materials is inevitable for the growth of the adherent cells. The suspension cells have been used as a main target to develop mass-production methods since it is easy to maintain the maximal cell density per unit volume for scale-up in the suspension cells.

Chinese hamster ovary (CHO) cell used in production of the biotechnology drugs is originally adherent cells, but can be adapted into suspension cultures. In the adherent cells adapted into the suspension cultures, there are some advantages of facilities of the scale-up and cell concentrations with higher density. However, the nutritions and oxygens are not supplied to the cells due to cell clusters generated during cell culture, and most adherent cells are not adapted in the suspension cultures in general. Therefore, an efficient method and system for mass-producing the adherent cell has not been developed yet, and thus industrialization using the adherent cells is not facile.

A predetermined space for culturing cells, a culture solution for supplying nutritions to them, and the various gases are required for cell culture. Certainly, it is also the same in the plant cells.

Particularly, the culture solutions and the various gases are introduced into the culture space and used for culturing cells, following the periodical exchange with new ones to maintain the cell tissues in a fresh condition.

Therefore, a cell culture device is essentially provided with a construction to supply and discharge the culture solutions and the various gases continuously and smoothly.

For the exchange of the culture solutions, a method utilizes a pipet to suck the culture solutions, to introduce and discharge them into the culture space. However, it is inefficient due to a possibility involving the cells in discharged culture solution and a difficulty of smooth exchange of the culture solution.

According to another conventional method, there is a method that the culture space is provided with an inlet port at one side thereof through which a predetermined amount of culture solution is introduced by an automatic or manual system, and with an outlet port at the other side thereof through which the culture solution used is discharged in the same manner.

In this method, a foreign substance could be introduced through the inlet port or the outlet port, thereby contaminating the cells. This method is also inconvenient because a user always participates in operation of the cell culture device. Furthermore, the mass cell culture is impossible due to the low efficiencies of the surface area caused from the use of the single device.

Furthermore, it is required to make a lot of time and effort for massive cell culture and it is hard to determine the collection time of the cells because of the difficulties in observing their growth status.

DETAILED DESCRIPTION OF THE INVENTION

It is an object of the present invention to provide a cell culture apparatus in which cells is easily cultured without much time and effort by using an automatic system and the collection time of the cells is determined by the observation of the cell culture apparatus, and a mass automatic cell culture device having it.

To achieve the above object, the present invention provides a cell culture apparatus, comprising: a cylindrical cell culture flask which is air-tightly sealed to culture a cell using a culture solution and various gases and formed of a transparent material to observe an internal portion thereof; an injection unit for supplying the cell and the culture solution into the cell culture flask; a collection unit for discharging the cells and the culture solution from the cell culture flask; and a cell culture flask receiving part which is comprised of first and second vertical frames in which a plurality of injecting parts and collecting parts for respectively receiving the injection unit and the collection unit are vertically formed to be opposed to each other, and plate type connection parts for receiving cell culture flasks, which are respectively disposed between upper ends and lower ends of the two opposed vertical frames to be spaced apart from each other in regular intervals, thereby connecting the first and second vertical frames, wherein injecting parts and collecting parts are aligned along the first and second vertical frames, respectively, and are empty cylindrical-shaped spaces which provide rooms for a reciprocating action of injection units and the collection units, wherein the first vertical frame is connected with the second vertical frame through plate-shaped connection parts.

Preferably, the cell culture flask is formed into a cylindrical shape with a predetermined height and comprises a culture space for cell culture, and at a side surface of the cell culture flask is formed a culture solution inlet port for introducing the culture solution or the cell into the culture space, a culture solution outlet port for discharging the culture solution or the cell from the culture space, gas inlet port and gas outlet port to introduce and discharge the various gases into/from the culture space, and a foreign substance inlet port for introducing a foreign substance.

Preferably, the foreign substance inlet port is opened and closed by a cap-type stopper.

Preferably, the cell culture flask is formed of a transparent plastic such as lexan and acryl, or a non-fragile tempered glass.

Preferably, the collection part of the cell culture flask is formed of a transparent plastic such as lexan and acryl, or a stainless steel.

Preferably, the injection units and the collection units comprise: (i) a syringe part with a power supply; (ii) a culture solution storing part which is connected with the syringe part, wherein the culture solution storing part is formed into a cylindrical shape for receiving the culture solution; (iii) a contact part which is connected with the culture solution storing part and contacted with the culture solution inlet port or the culture solution outlet port of the cell culture flask to flow the culture solution, wherein a contact part is formed at an end of the syringe part and has a funnel-shaped; (iv) a piston member which is disposed to be reciprocated in the culture solution storing part; and (v) a connection member of which one end is connected with the piston member and the other end is connected with the power supply.

Preferably, the connection member comprises a linear rod or a lead screw.

Preferably, the power supply part comprises a motor which is operated by electric power supplied through a cable from an outside.

To achieve another object, there is provided a mass automatic cell culture device, comprising: a hexahedral main body which has an empty space therein and a door to open and close one surface thereof; a rotation driving device which is provided at a bottom surface of the empty space of the main body and makes a rotary motion; a cell culture apparatus including a cylindrical cell culture flask which is air-tightly sealed and formed of a transparent material, an injection unit for supplying the cell and the culture solution into the cell culture flask, a collection unit for discharging the cells and the culture solution from the cell culture flask, and a cell culture flask receiving part which is comprised of first and second vertical frames in which a plurality of injecting parts and collecting parts for respectively receiving the injection unit and the collection unit are vertically formed to be opposed to each other, and plate type connection parts which are respectively disposed between upper ends and lower ends of the two opposed vertical frames to be spaced apart from each other in regular intervals, thereby connecting the first and second vertical frames; a push unit which is provided with a plurality of semicircular plate type supports disposed on the connection part to cover a partial surface of the cell culture flask, a plurality of first robot arms which are respectively coupled to a side surface of each support and reciprocated forward and backward to move the supports forward and backward, and a driving part which receives ends of the plurality of the first robot arms and separately operates the first robot arms; and an observation unit which is provided at an end of second robot arms that are vertically reciprocated on a vertical frame disposed at one side of the rotation driving device, wherein the cell culture flask provided on the supports is independently protruded to an outside by the first robot arm of the push unit.

Preferably, the mass automatic cell culture device further comprises: a temperature controlling part which is provided at one side of the main body to control an internal temperature of the main body; a gas supplying part which is provided at one side of the main body to supply gas to the cell culture apparatus; an ultraviolet radiating unit which is provided on an internal upper surface of the main body to supply the ultraviolet light; and a bottle-shaped culture storing part which is connected through a tube to the injection unit or the collection unit of the cell culture apparatus to temporarily store the culture solution.

Preferably, the observation unit comprises a CCD camera of which magnification is controlled.

Preferably, the temperature controlling part comprises: a fan which is provided at one side of the main body to supply an external air to the main body; a HEPA filter which is disposed at an internal surface of the main body to be adjacent to the fan and purifies the external air supplied from the fan; a heat pipe which is disposed to be adjacent to the HEPA filter and supplies heat to the external air purified by the HEPA filter; a temperature sensor which is disposed at one side of the main body to measure the internal temperature of the main body; and a control part which operates the fan and the heat pipe when the temperature received from the temperature sensor is lower than the preset temperature.

Preferably, the rotation driving device comprises: a power supplying part which is operated by receiving electric power from an outside; a rotational part which is rotated by the power supplying part; and a driving part which is disposed at an upper side of the rotational part so that only an inclination thereof is changed to be corresponding to a rotational direction of the rotational part in a stopped state when the rotational part is rotated.

Preferably, the rotational part comprises: a rotational shaft of which one end is coupled to the power supplying unit to be rotated by the power supplying part; a circular plate type first supporting part which is disposed at a lower end of the rotational shaft to rotatably support the rotational shaft; a first supporting part fixing portion which is provided at a lower side of the first supporting part to fix the first supporting part to the rotational shaft; a circular plate type second supporting part which is disposed at an upper side of the first supporting part to be connected with the first supporting part through a plurality of hinge members and which is formed with an opening at a center portion thereof; a ball bearing receiving part which is provided on circumference of an upper surface of the second supporting part and formed with a spherical recessed portion to receive a part of the ball bearing; and a ball bearing which is received in the ball bearing receiving part to be rolled.

Preferably, the driving part has a circular plate shape for mounting the cell culture apparatus, and a member with a spherical recessed portion in which the spherical end of the rotational shaft of the rotational part is pivotably inserted is provided at the internal surface of the circular plate in a form of the sphere.

Preferably, the power supply part is a motor which is operated by electric power supplied from an outside.

Preferably, the hinge member is disposed in which a central axis thereof is positioned at a center portion of both contacting portions, and thus the hinge member can be freely pivoted in both directions.

Preferably, the door comprises a handle, a rod-shaped member which is contacted with the side combined to the main body by a link, and a guide member which is provided on an external upper surface of the main body to open and close the rod-shaped member of the door.

Preferably, the cell culture flask is formed of a transparent plastic such as lexan and acryl, or a non-fragile tempered glass.

Preferably, the cell culture flask is formed of a transparent plastic such as lexan and acryl, or stainless steel.

Preferably, the injection units and the collection units comprise: (i) a syringe part with a power supply; (ii) a culture solution storing part which is connected with the syringe part, wherein the culture solution storing part is formed into a cylindrical shape for receiving the culture solution; (iii) a contact part which is connected with the culture solution storing part and contacted with the culture solution inlet port or the culture solution outlet port of the cell culture flask to flow the culture solution, wherein a contact part is formed at an end of the syringe part and has a funnel-shaped; (iv) a piston member which is disposed to be reciprocated in the culture solution storing part; and (v) a connection member of which one end is connected with the piston member and the other end is connected with the power supply.

Preferably, the connection member comprises a linear rod or a lead screw.

Preferably, the power supply part is a motor which is operated by electric power supplied through a cable from an outside.

According to Examples of the present invention described above, cells is mass-produced and easily cultured without much time and effort by using an automatic system and the collection time of the cells is determined by observing the growth state of the cells in the cell culture apparatus using a cell culture apparatus and a mass automatic cell culture device having it.

<Detailed Description of Main Elements>

Figure 1:
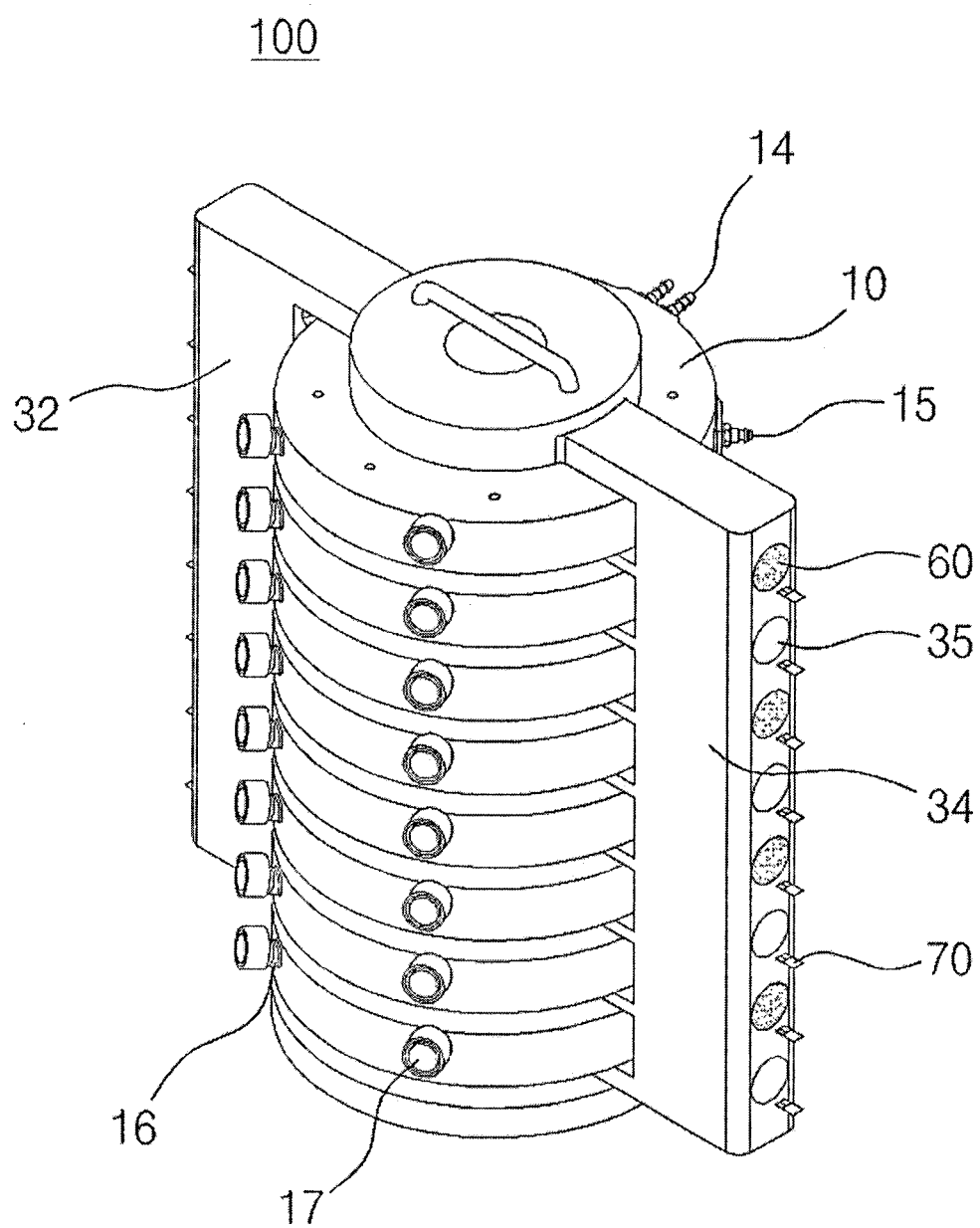
FIG. 1 is a perspective view of a cell culture flask according to an embodiment of the present invention.

10: cell culture flask
11: culture space
12: culture solution inlet port
13: culture solution outlet port
14: gas inlet port
15: gas outlet port
16: foreign substance inlet port
17: stopper
30: cell culture flask receiving part
32: first vertical frames
33: injecting part
34: second vertical frames
35: collecting part
36: connection part
50: injection unit
60: collection unit
70: cable
100: cell culture apparatus
110: main body
115: door
120: rotation driving device
130: push unit
134: first robot arm
140: observation unit
150: ultraviolet radiating unit
160: temperature controlling part
170: gas supplying part
180: culture storing part
190: liquid crystal display
200: mass automatic cell culture device

EXAMPLES

The objects, characters or other advantages of this invention described above will become apparent to those skilled in the art by explaining the preferable Examples of the present invention in detail referring to the appended drawings. The cell culture apparatus and the mass automatic cell culture device having it according to the Examples of the present invention will be described in further detail together with the appended claims and drawings below.

FIG. 1 is a perspective view of a cell culture apparatus (100) according to an embodiment of the present invention.

As shown in FIG. 1, the cell culture apparatus (100) according to an embodiment of the present invention includes cylindrical cell culture flasks (10) which are air-tightly sealed to culture a cell using a culture solution and the various gases and formed of a transparent material to observe an internal portion thereof, injection units (50) for supplying the cell and the culture solution into the cell culture flask (10), collection units (60) for discharging the cells and the culture solution from the cell culture flask (10), and a cell culture flask receiving part (30) which is comprised of vertical frames (each 32, 34) in which a plurality of injecting parts and collecting parts for respectively receiving injection units and collection units are vertically formed to be opposed to each other, and plate type connection parts (36) which contact the space between the upper end and lower end of the two vertical frames in a constant interval.

Figure 2:
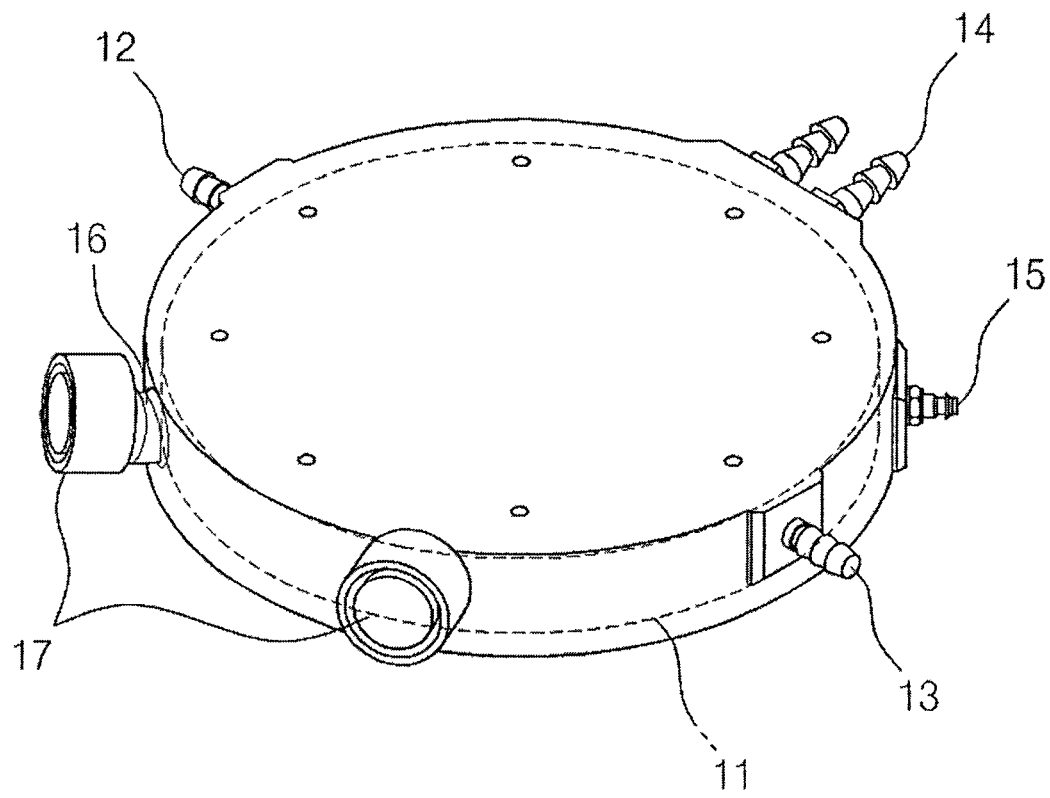
FIG. 2 is a perspective view of the cell culture flask shown in FIG. 1
Figure 3:
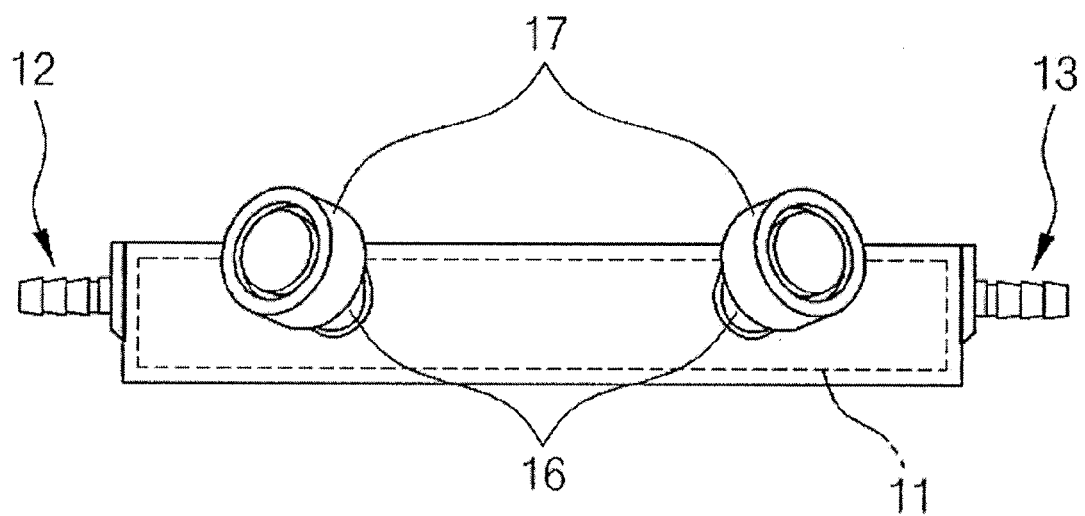
FIG. 3 is a front view of the cell culture flask shown in FIG. 1.

FIG. 2 is a perspective view of the cell culture flask (10) shown in FIG. 1, and FIG. 3 is a front view of the cell culture flask (10) shown in FIG. 1. In FIGS. 2-3, the cell culture flask (10) is formed into a cylindrical shape with a predetermined height and comprises a culture space (11) for cell culture, at a side surface of the cell culture flask (10) is formed a culture solution inlet port (12) for introducing the culture solution or the cell into the culture space (11), a culture solution outlet port (13) for discharging the culture solution or the cell from the culture space (11), gas inlet port (14) and gas outlet port (15) to introduce and discharge the various gases into/from the culture space (11), respectively, and a foreign substance inlet port (16) for introducing a foreign substance.

Generally, the culture space (11) provided at the cell culture space (10) has a flat surface without irregular or inclined portions. Otherwise, a part of the culture space (11) has an inclined surface.

The culture solution inlet port (12) and outlet port (13) are formed to be protruded from an outer surface of the cell culture flask (10), and they may have a narrow end. The narrow end prevents a foreign substance from being introduced into the culture space (11) and the culture solution from being leaked out where the culture solution is not flowed through the culture solution inlet port (12) and outlet port (13).

The culture solution inlet port (12) and the culture solution outlet port (13) are provided in plural according to the necessity.

Preferably, the culture solution inlet port (12) and outlet port (13) are disposed to be opposed to each other, dividing a flow direction of the culture solution to supply or discharge the culture solution. In the culture solution inlet port (12) and outlet port (13) disposed to be adjacent to each other, the culture solution may be flowed into the culture solution inlet port (12) where the culture solution inlet port (12) is opened to supply the culture solution. On the other hand, the culture solution inlet port (12) and outlet port (13) are disposed to be adjacent to each other where there is no such possibility.

The gas inlet ports (14) and gas outlet ports (15) are formed to be protruded from the outer surface of the cell culture flask (10), and they may have a narrow end. The gas inlet ports (14) and gas outlet ports (15) are provided in plural, separately from the culture solution inlet port (12) and outlet port (13).

In the animal cells cultured in the cell culture flask (10), $O_2$ supply is needed and $CO_2$ supply is required in the plant cells. These gases can be supplied through the gas inlet port (14). Meanwhile, $N_2$ or other gases can be supplied.

Normal gas supply and discharge is essential to maintain the cell cultured in the cell culture flask (10) in a fresh condition. Therefore, the gas outlet port (15) for discharging the gas supplied inside the cell culture flask to an outside is provided.

In a disposable cell culture flask (100), since a predetermined amount of culture solution and gas is supplied to the cell culture flask and then grown cells are harvested, the gas outlet port (15) is not separately needed. In a cell culture flask (10) used repeatedly, the gas outlet port (15) is required to maintain the cells in the fresh condition and an internal portion of the cell culture flask (10) in a clean condition.

The gas outlet port (15) is also used to supply the gas excessive or to remove gas generated from the cells per se.

To grow the cells normally, the foreign substance inlet port (16) for supplying a foreign substance can be separately provided. The foreign substance inlet port (16) is provided with a cap-type stopper (17) for opening and closing. The stopper (17) may be a general rubber stopper. The collecting tools such as a pipet can be used where the foreign substance is introduced through the foreign substance inlet port (16).

A user can collect a necessary amount of cells through the foreign substance inlet port (16). The pipet can be also used.

The cell culture flask (10) shown in FIGS. 1-3 is formed of a transparent material for the researcher to observe a growth level of the cells from the outside. The transparent material includes a transparent plastic such as lexan and acryl. Preferably, the transparent material is a non-fragile tempered glass.

The cell culture flask (10) represented in FIGS. 1-3 has a cylindrical shape, but it is possible to be other shapes such as a rectangular parallelepiped structure and a polyhedral structure. On the other hand, the cell culture flask (10) formed of the cylindrical shape has a wide culture space and a high strength against external impact and is facilely moved due to the absence of its corner portion.

Figure 4:
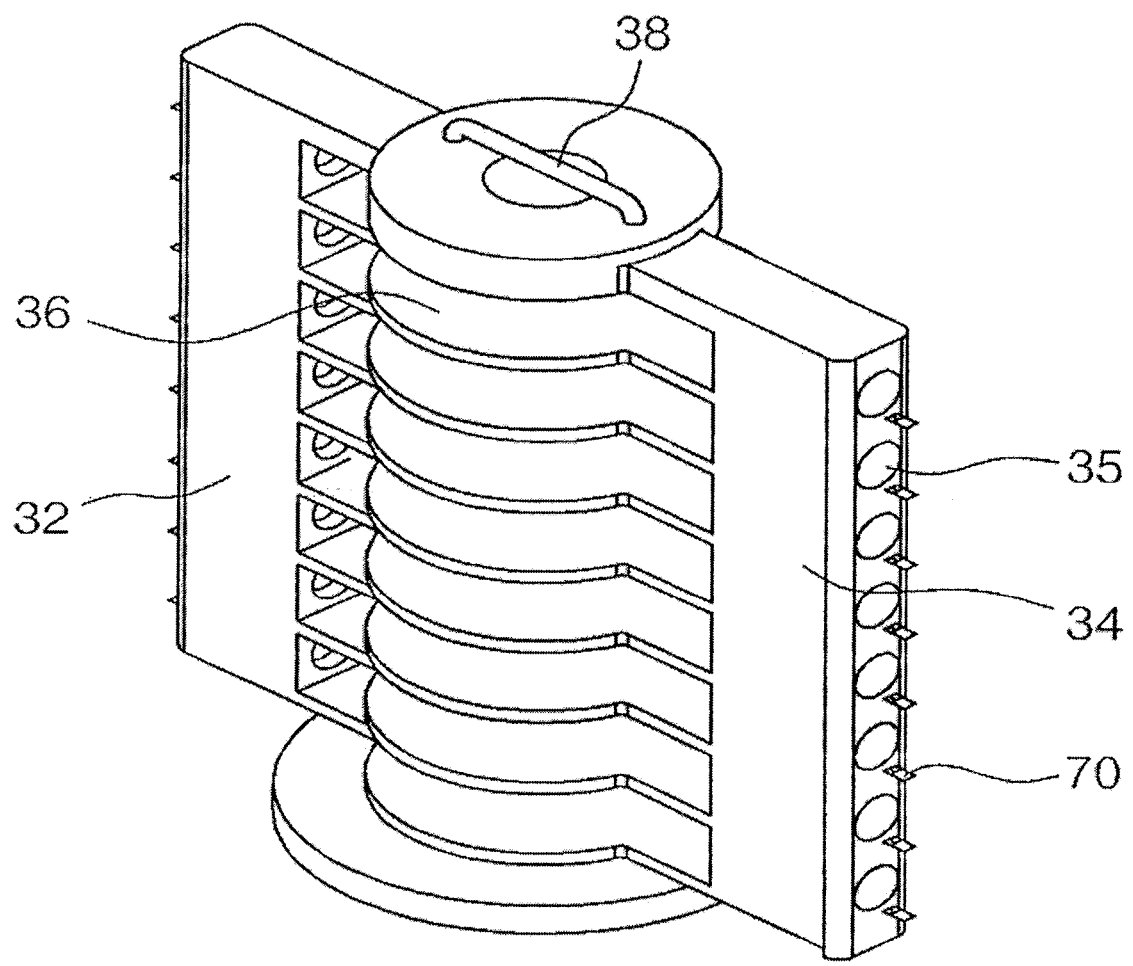
FIG. 4 is a perspective view of a cell culture flask receiving part according to an embodiment of the present invention.

FIG. 4 is a perspective view of a cell culture flask receiving part (30) according to an embodiment of the present invention.

The cell culture flask receiving part (30) for receiving the cell culture flask (10) includes vertical frames (each 32, 34) in which a plurality of injecting parts (33) and collecting parts (35) for respectively receiving injection units and collection units are vertically formed to be opposed to each other, and plate type connection parts (36) which contact the space between the upper end and lower end of the two vertical frames in a constant interval.

In the injecting parts (33) and the collecting parts (35) divided from each other, the vertical frames (each 32, 34) are disposed to be adjacent to each other. In addition, each vertical frame may be vertically disposed to the connection part (36).

Each axial length of the vertical frames (each 32, 34) is changed according to the number of injecting parts (33) and collecting parts (35).

The injecting parts (33) and the collecting parts (35) are formed to be corresponding to outer shapes of the injection unit (50) and the collection unit (60) to install the injection unit (50) and the collection unit (60).

The plate type connection part (36) has a circular center portion to stably support the cell culture flask (10). To stably receive the cell culture flask (10) by the plate type connection part (36), it may use other structure such as a rod structure instead of the plate structure.

The interval between the connection parts (36) is determined by a height of the cell culture flask (10) for installation of the cell culture flask (10).

A handle (38) is provided at an uppermost surface of the cell culture flask receiving part (30). Therefore, the cell culture flask receiving part (30) is stably and facilely transported by the handle (38) without separation of each cell culture flask (10).

The cell culture flask receiving part (30) is formed of a transparent material such as lexan and acryl to observe a growth level of the cells from the outside or a stainless steel to prevent corrosions.

Figure 5:
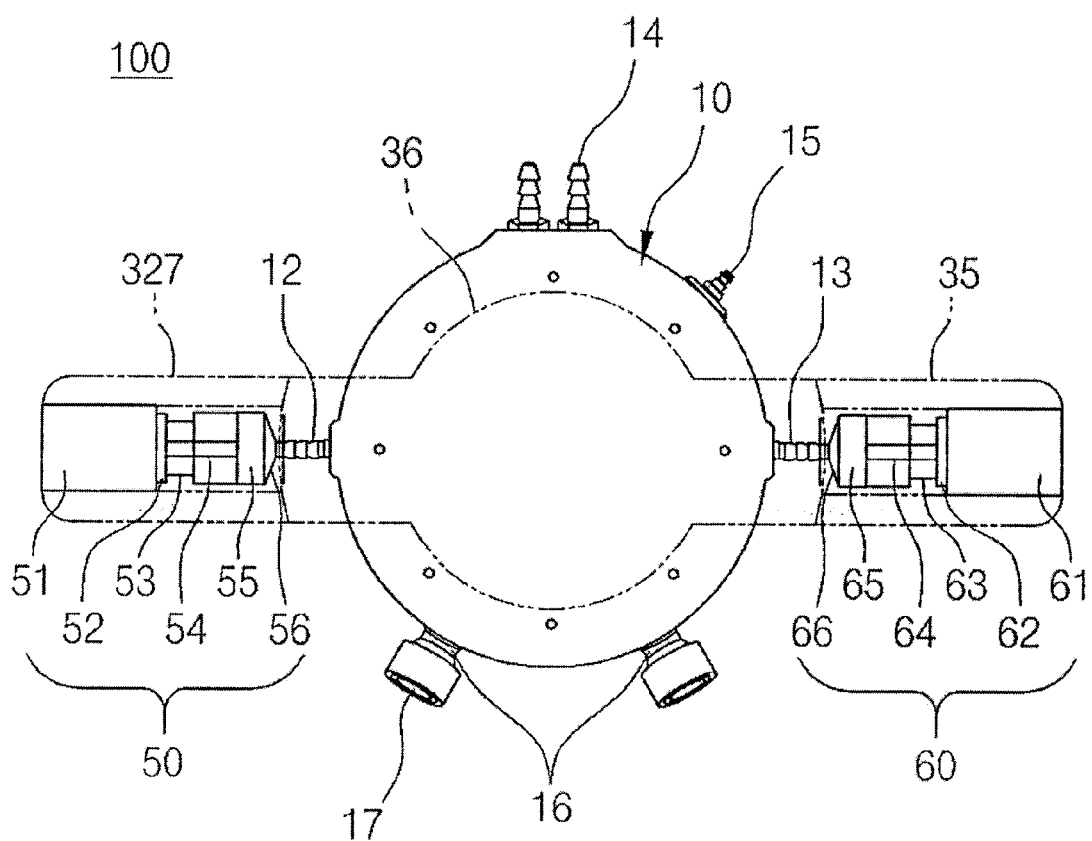
FIG. 5 is a plane view of a cell culture apparatus according to an embodiment of the present invention.

FIG. 5 is a plane view of the cell culture apparatus (100) in which the cell culture flask (10), the injection unit (50) and the collection unit (60) are provided in the cell culture flask receiving part (30).

The injection unit (50) and the collection unit (60) are constituted as a form of a syringe as a whole. The injection unit (50) and the collection unit (60) include a syringe part (51, 61) with a power supply part (52, 62), a culture solution storing part (53, 63) which is connected with the syringe part (51, 61) and receives the culture solution, a contact part (56, 66) which is connected with the culture solution storing part (53, 63) and contacted with the culture solution inlet port (12) or the culture solution outlet port (13) of the cell culture flask (10) to flow the culture solution, a piston member (55, 65) which is reciprocated inside the culture solution storing part (53, 63), and a connection member (54, 64) of which one end is connected with the piston member (55, 65) and the other end is connected with the power supply part (52, 62).

The injection unit (50) and collection unit (60) can be connected with or separated from the cell culture flask (10) and also detachable from the cell culture flask receiving part (30). In other words, only the cell culture flask (10) is normally coupled to the cell culture flask receiving part (30). To supply or discharge the culture solution, the injection unit (50) or collection unit (60) is coupled to the injecting part (33) or collecting part (35) of the cell culture flask receiving part (30).

The small power supply part (52, 62) is provided in the syringe part (51, 61), in which a detachable motor which is operated by electric power supplied through a cable (70) from an outside is used. Other units such as a electromotor or a pump are also used as the power supply part (52, 62).

The connection member (54, 64) comprises a linear rod which is simply reciprocated, or a lead screw which is reciprocated during the rotation. However, in the lead screw used as the connection member (54, 64), it is operated by rotational force of the motor.

Instead of using the power supply part like the motor, a user can grasp an outer end portion of the connection member (54, 64) and apply force, generating that the connection member (54, 64) is moved. In the cell culture not to mass-produce cells but to obtain a small amount of particular cells for experiments, the user can directly operate the connection member (54, 64) to collect the culture solution or the cells.

The culture solution storing part (53, 63) connected with the syringe part (51, 61) stores the culture solution flowed by the piston member (55, 65).

The contact part (56, 66) connected with the culture solution storing part (53, 63) functions as a passage to flow the culture solution by contact to the culture solution inlet port (12) or the culture solution outlet port (13) of the cell culture flask (10).

The contact part (56, 66) is formed into an end part of the syringe (e.g., a funnel) so that a hole through which the culture solution is passed becomes narrow, thereby increasing a flow rate of the culture solution.

It is possible to facilely supply and discharge the culture solution by providing an auto control unit to the injection unit (50) and the collection unit (60), or to the gas inlet port (14) and the gas outlet port (15).

Figure 6:
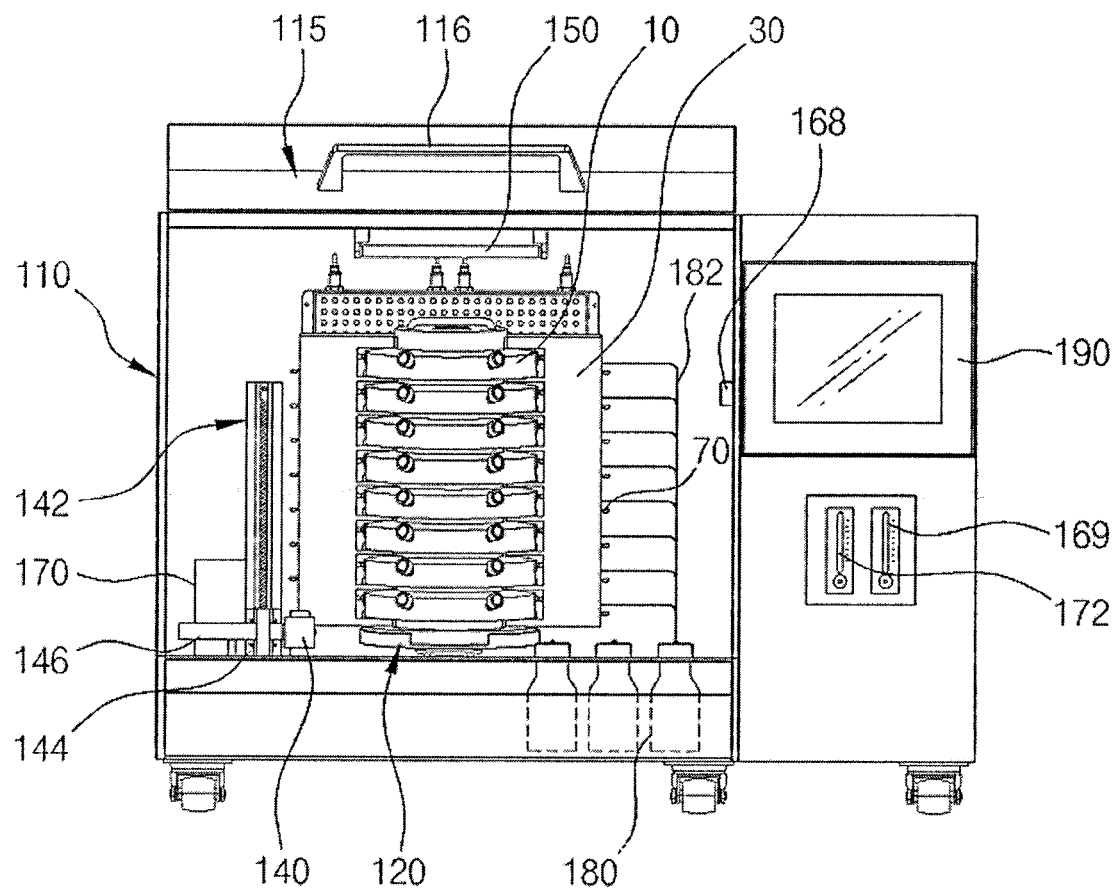
FIG. 6 is a front view of a mass automatic cell culture device according to an embodiment of the present invention.
Figure 7:
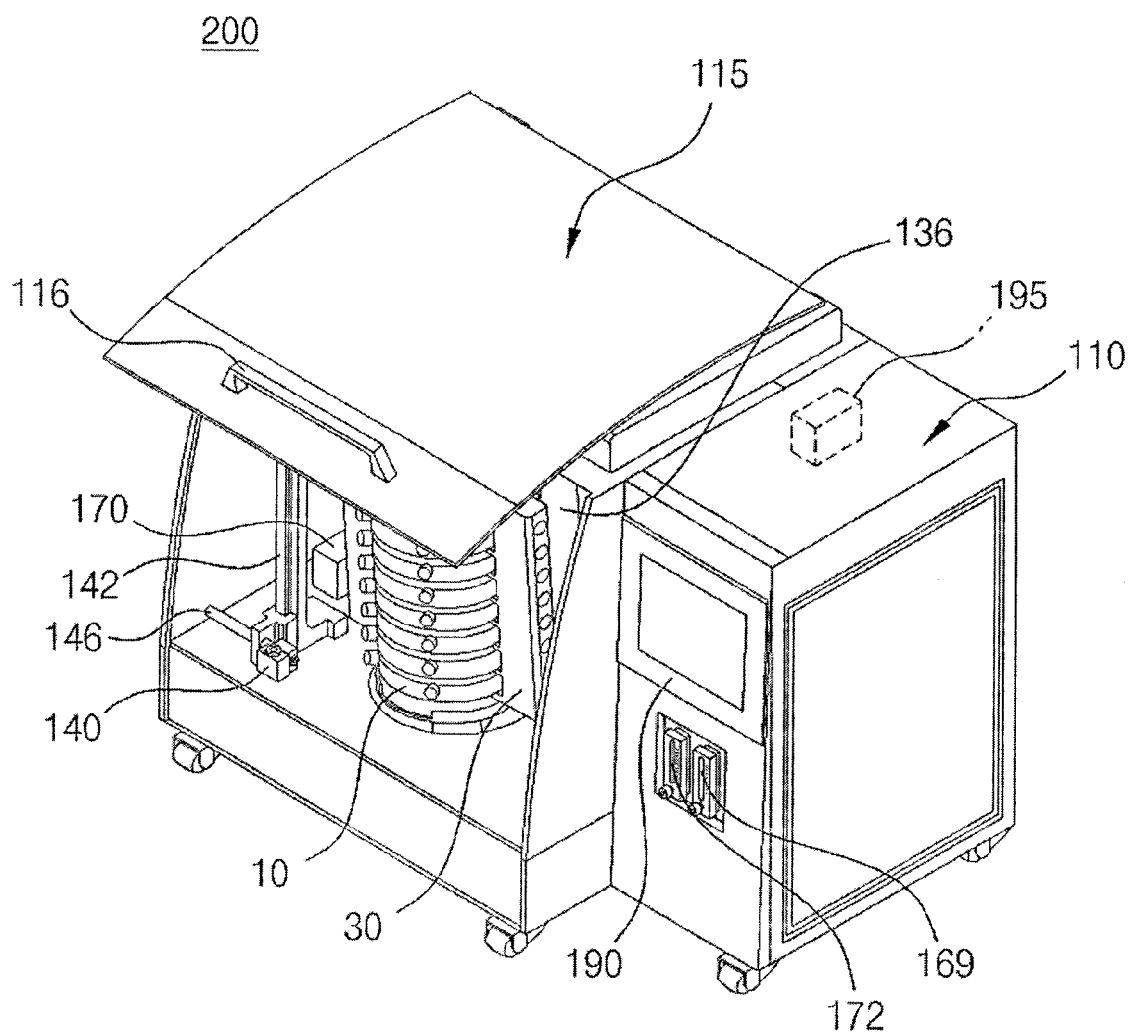
FIG. 7 is a perspective view of the mass automatic cell culture device shown in FIG. 6.
Figure 8:
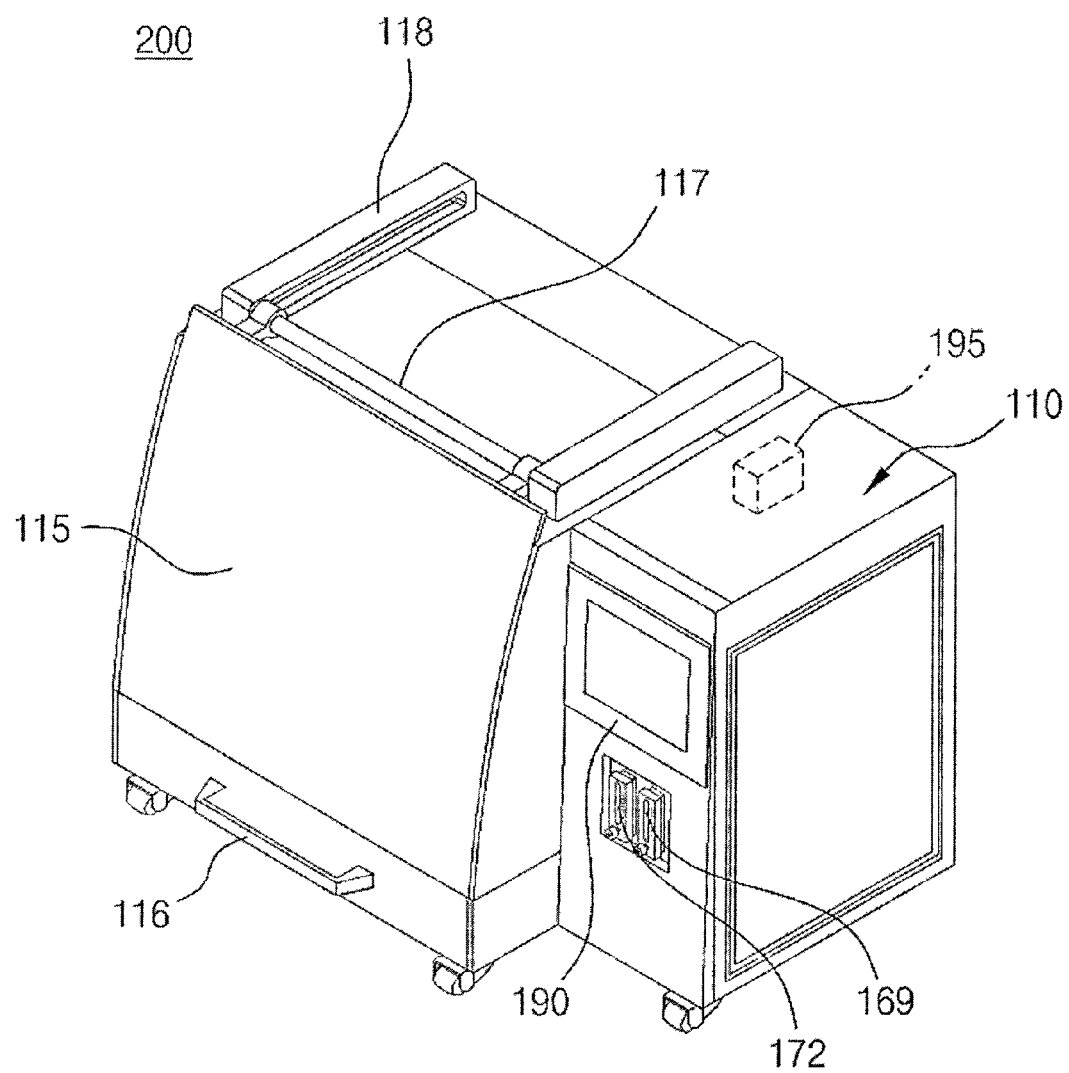
FIG. 8 is a perspective view showing a status that a door of the mass automatic cell culture device shown in FIG. 6 is closed.

FIG. 6 is a front view of a mass automatic cell culture device (200) according to an embodiment of the present invention, FIG. 7 is a perspective view of the mass automatic cell culture device (200) shown in FIG. 6, and FIG. 8 is a perspective view showing a status that a door (115) of the mass automatic cell culture device (200) shown in FIG. 6 is closed.

Given to FIGS. 6-8, the mass automatic cell culture device (200) according to an embodiment of the present invention includes a hexahedral main body (110) which has an empty space therein and a door (115) to open and close one surface thereof, a rotation driving device (120) which is provided at a bottom surface of the empty space of the main body and makes a rotary motion, a cell culture apparatus (100) including a cylindrical cell culture flask (10) which is air-tightly sealed and formed of a transparent material, a cell culture apparatus installing the cell culture flask (10), the injection unit (50) and the collecting unit (60) in the cell culture flask receiving part (30), a push unit which is provided with a plurality of semicircular plate type supports (132) disposed on the connection part (36) of a cell culture flask receiving part (30) to cover a partial surface of the cell culture flask (10), a plurality of first robot arms (134) which are coupled to a side surface of each support (132) and reciprocated to move the supports (132) forward and backward, and a driving part (136) which receives ends of the plurality of the first robot arms (134) and independently operates the first robot arms (134), and an observation unit (140) which is provided at an end of second robot arms (146) that are vertically reciprocated on a vertical frame (142) disposed at one side of the rotation driving device (120).

The cell culture apparatus includes cylindrical cell culture flasks (10) which are air-tightly sealed and formed of a transparent material, injection units (50) for supplying the cell and the culture solution into the cell culture flask (10), collection units (60) for discharging the cells and the culture solution from the cell culture flask (10), and a cell culture flask receiving part (30) comprising vertical frames (each 32, 34) in which a plurality of injecting parts (33) and collecting parts (35) for respectively receiving injection units (50) and collection units (60) are vertically formed to be opposed to each other, and plate type connection parts (36) which contact the space between the upper end and lower end of the two vertical frames (32, 34) in a constant interval;

The mass automatic cell culture device (200) further includes a temperature controlling part (160) which is provided at one side of the main body (110) to control an internal temperature of the main body, a gas supplying part (170) which is provided at one side of the main body (110) to supply gas to the cell culture apparatus (100), an ultraviolet radiating unit (150) which is provided on an internal upper surface of the main body (110) to supply the ultraviolet light, and a bottle-shaped culture storing part (180) which is connected through a tube (182) to the injection unit (50) or the collection unit (60) of the cell culture apparatus (100) to temporarily store the culture solution.

The door (115) of the mass automatic cell culture device (200) is provided with a handle (116), a rod-shaped member (117) which is contacted with the side combined to the main body (110) by a link, and a guide member (118) which is provided on an external upper surface of the main body (110) to open and close the rod-shaped member (117) of the door (115).

The cell culture apparatus (100) is already described in detail with reference to FIGS. 1-5, and thus the description thereof will be omitted.

Figure 9:
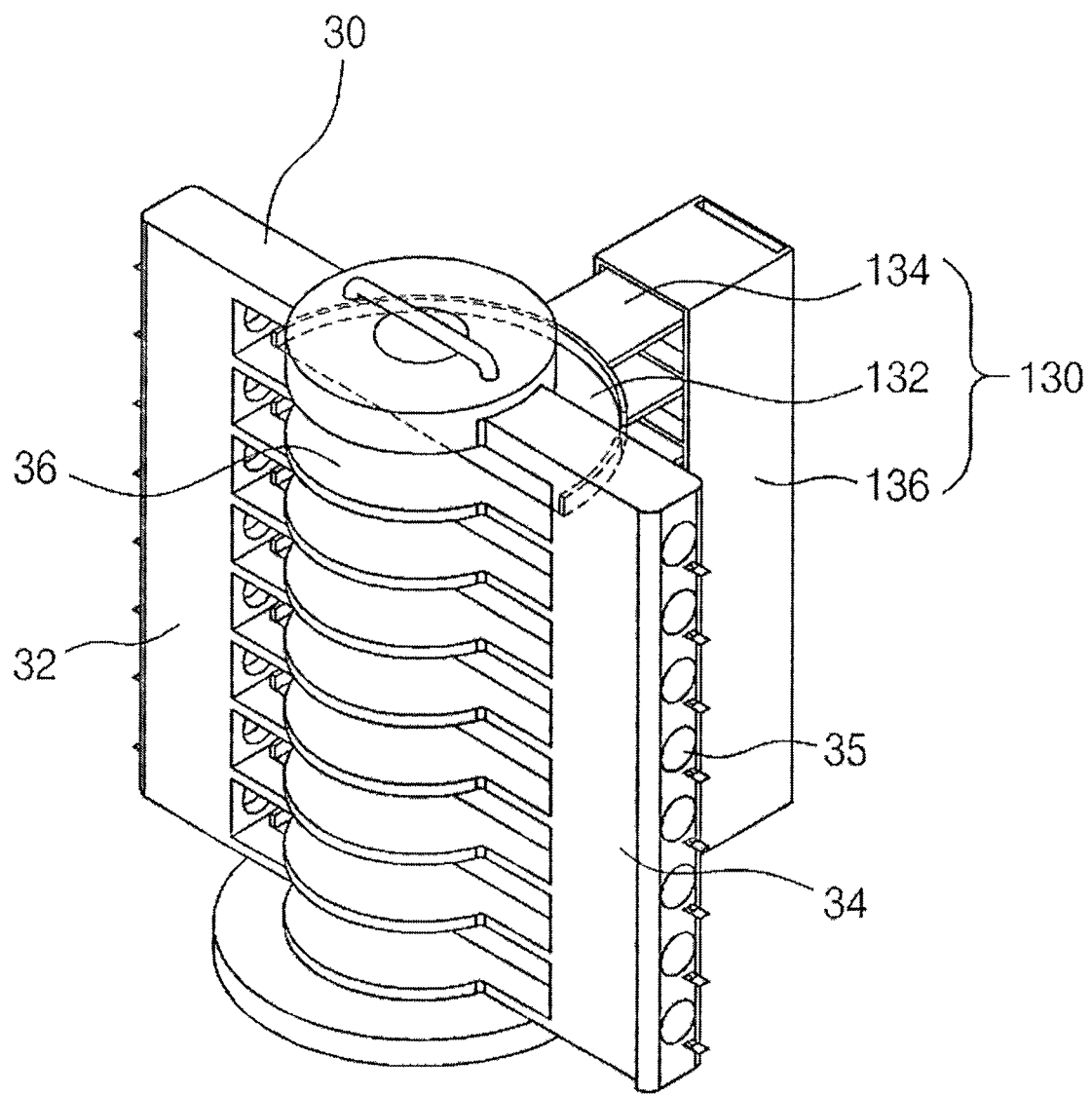
FIG. 9 is a perspective view of a push unit provided at the cell culture flask receiving part.
Figure 10:
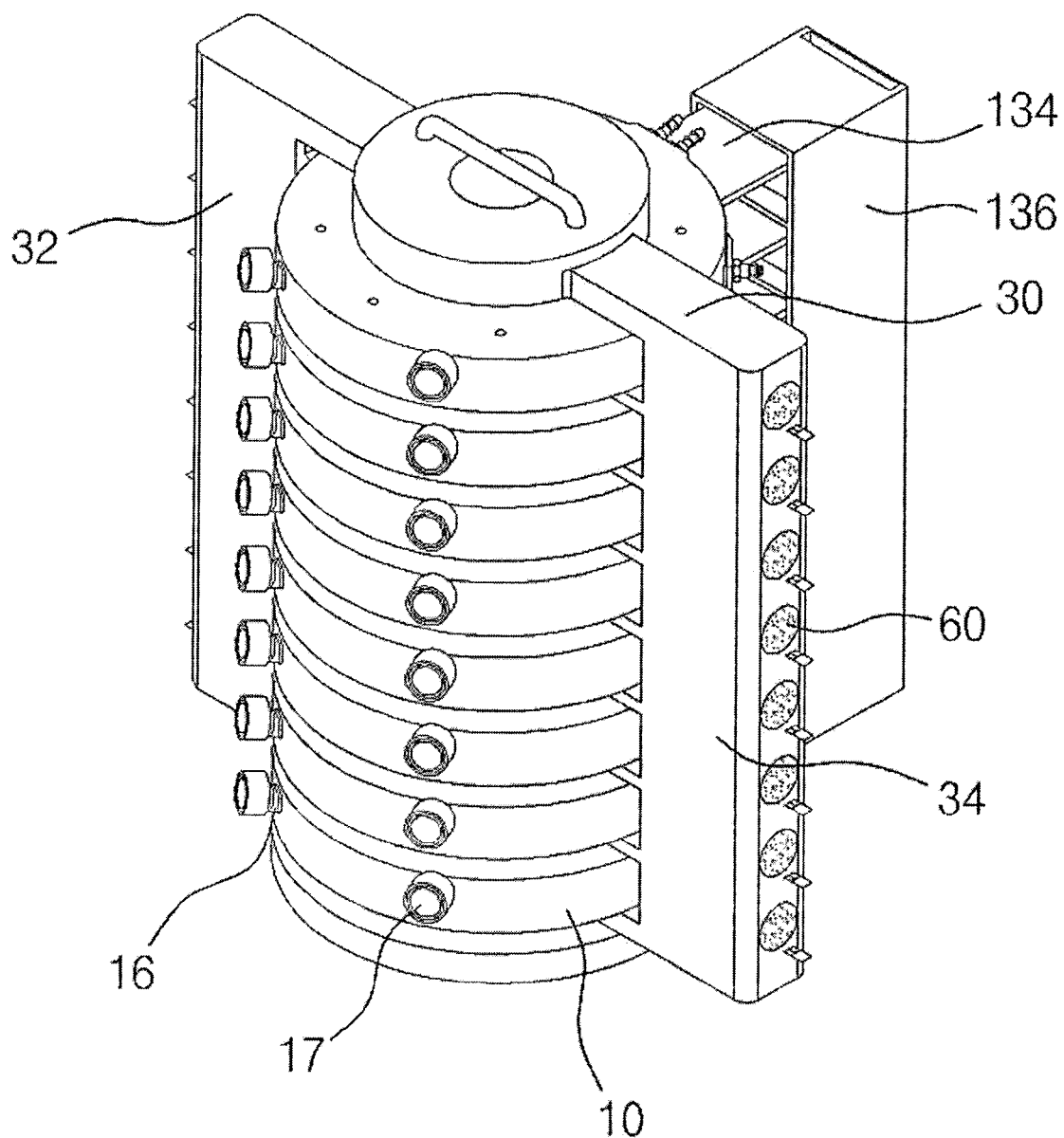
FIG. 10 is a perspective view of the push unit provided at the cell culture apparatus.
Figure 11:
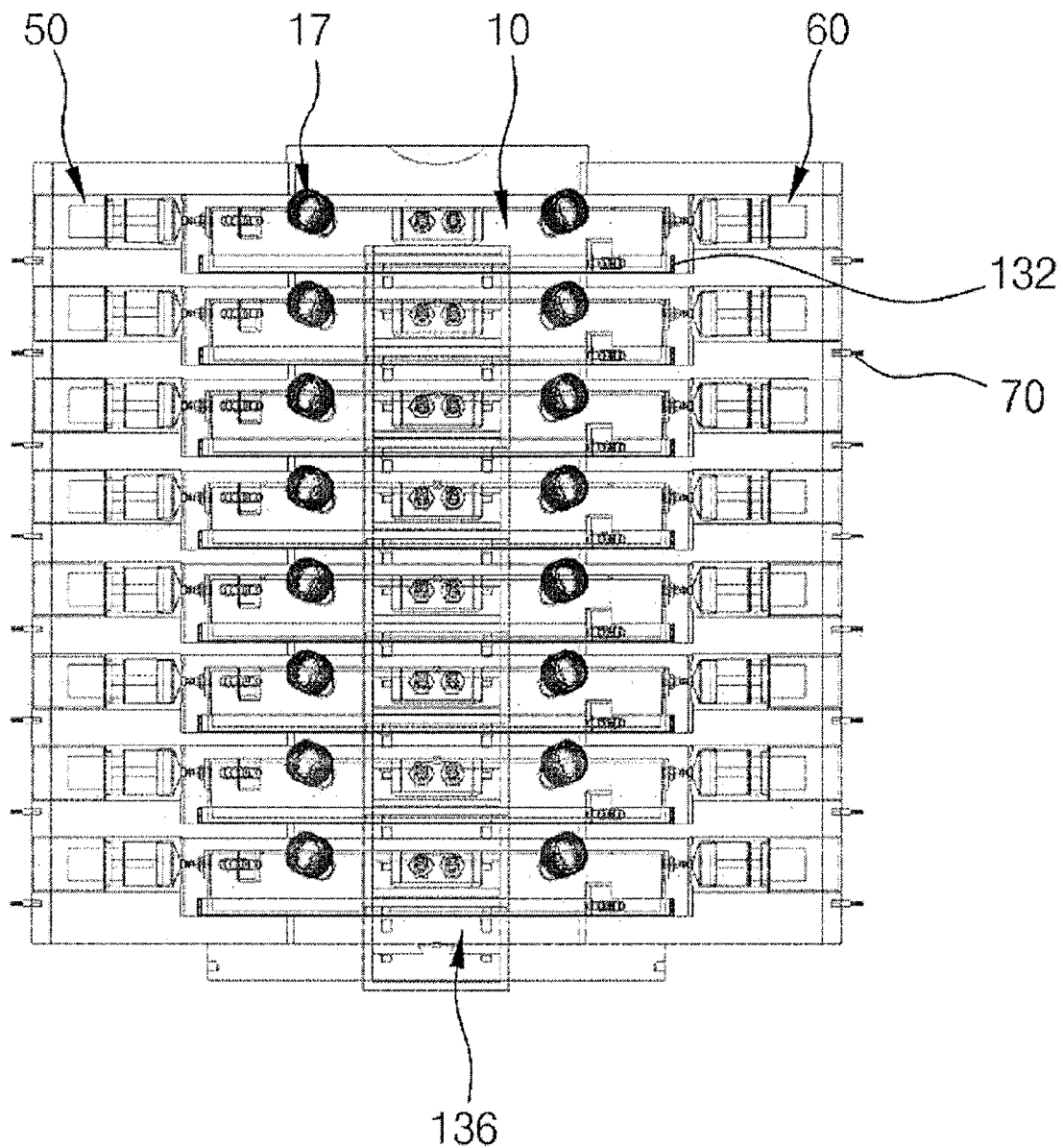
FIG. 11 is a front view of FIG. 10.

FIG. 9 is a perspective view of a push unit (130) provided at the cell culture flask receiving part (30), FIG. 10 is a perspective view of the push unit (130) provided at the cell culture apparatus (100), and FIG. 11 is a perspective front view of a push unit (130) shown in FIG. 10.

As shown in FIG. 9, the plurality of supports (132) which is attached to the ends of the plurality of first robot arms (134) provided at the driving device (136) of the push unit (130) are disposed on the upper surface of each of the connection parts (36) of the cell culture flask receiving part (30).

The plurality of first robot arms (134) is reciprocated forward and backward by operation of the driving device (136) of the push unit (130). One of the first robot arms (134) or the plurality of first robot arms (134) can be operated at the same time by the operation of the driving part (136). The driving part (136) can be operated by oil pressure.

Since the first robot arm (134) is repeatedly reciprocated, it is preferable that it is prepared as an abrasion-resistant material. Alternatively, it can be formed of a stainless steel to prevent corrosion.

FIG. 10 shows the cell culture apparatus (100) in which the cell culture flask (10), the injection unit (50) and the collection unit (60) are provided at the cell culture flask receiving part (30).

The first robot arm (134) is reciprocated forward and backward by operating the driving part (136) of the push unit (130), and thus the cell culture flask (10) put on the support (132) which is connected with the end of the first robot arm (134) is moved forward and backward along with the support (132).

In FIG. 11, the cell culture flask (10) is disposed on the support (132) of the push unit (130). A rectangular box which is vertically shown at a center portion of the drawing represents the driving part (136). The injection unit (50) and the collection unit (60) are equally formed in a form of a syringe, and the electric power was supplied to them through a cable (70).

Figure 12:
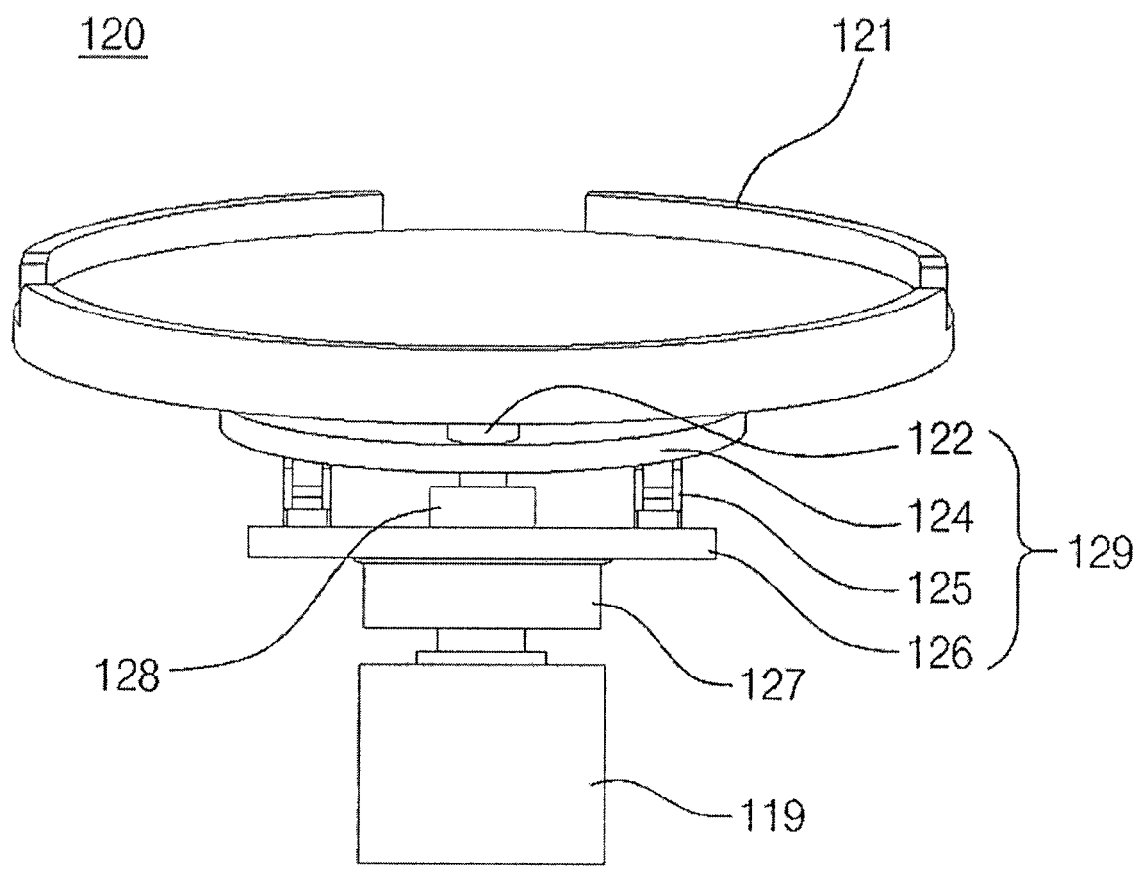
FIG. 12 is a perspective view of a rotation driving device according to an embodiment of the present invention.
Figure 13:
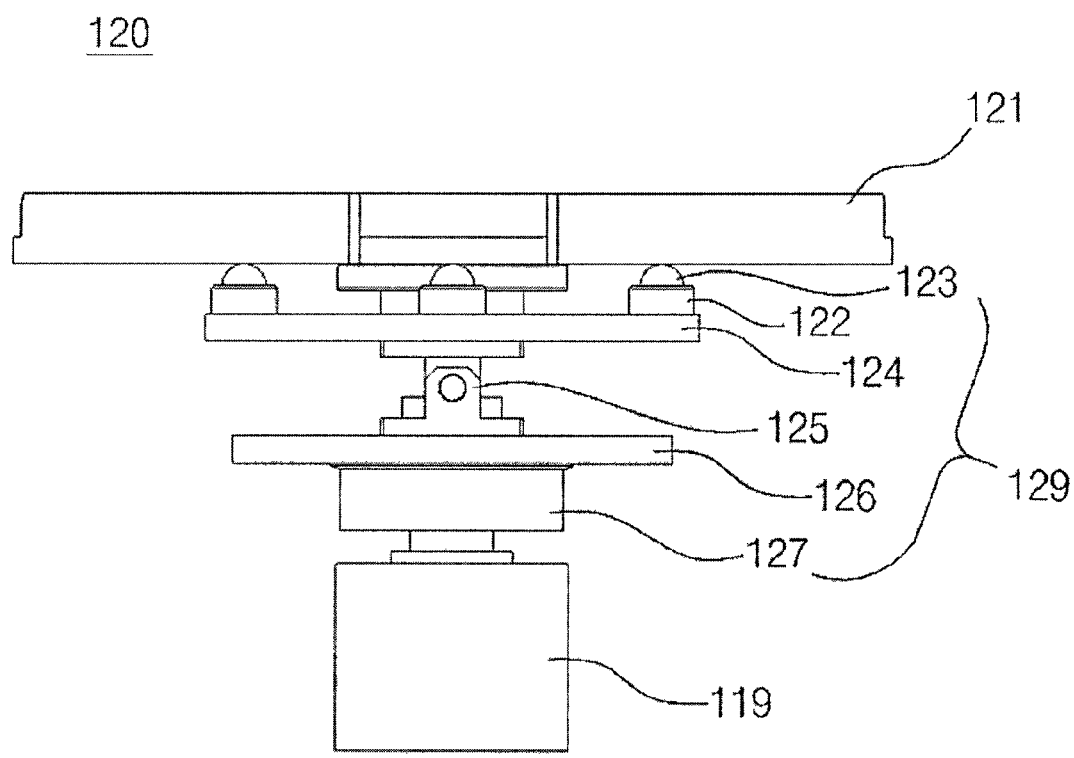
FIG. 13 is a front view of the rotation driving device according to the embodiment of the present invention.
Figure 14:
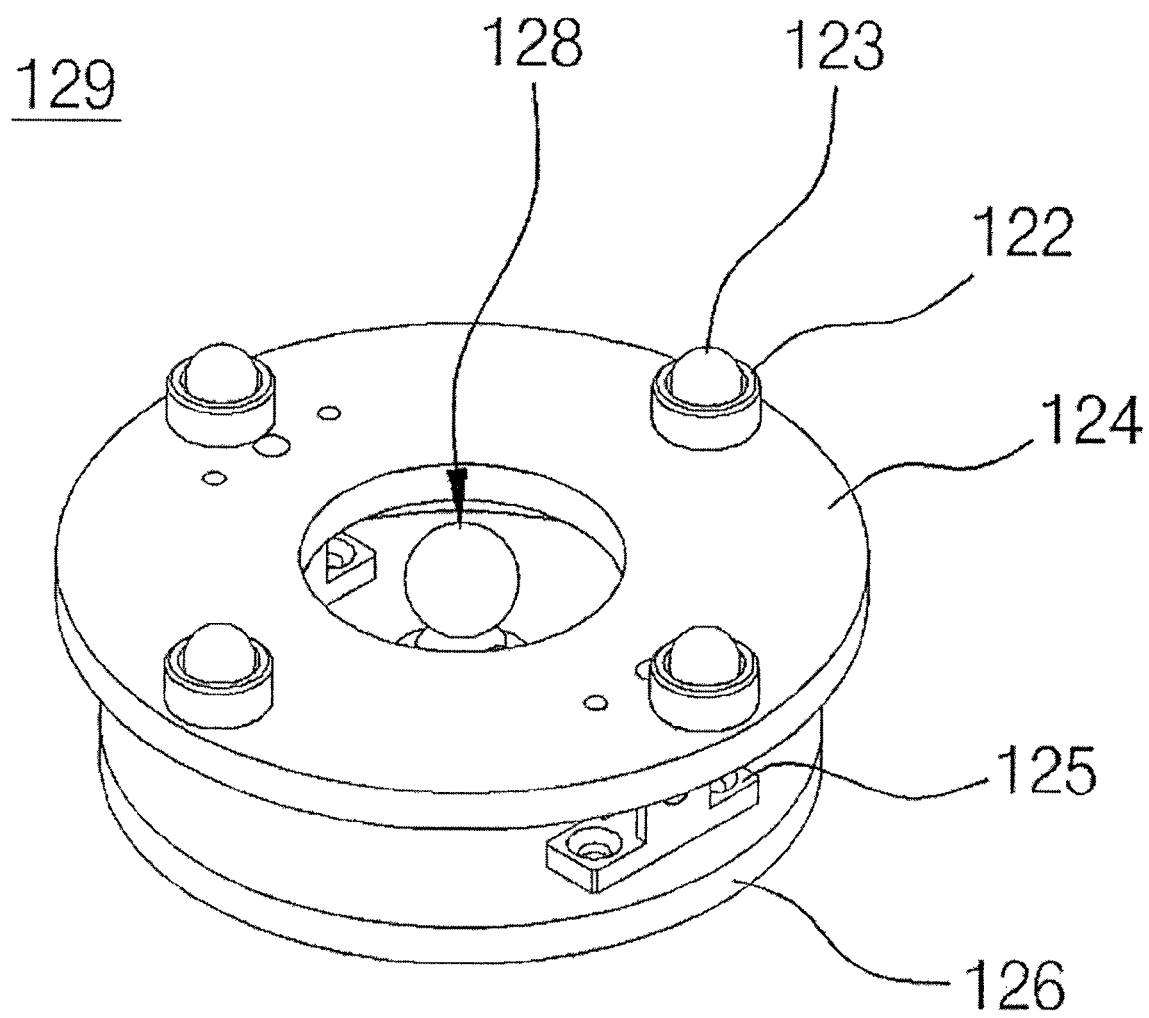
FIG. 14 is a perspective view of a rotational part provided at the rotation driving device shown in FIG. 13.
Figure 15:
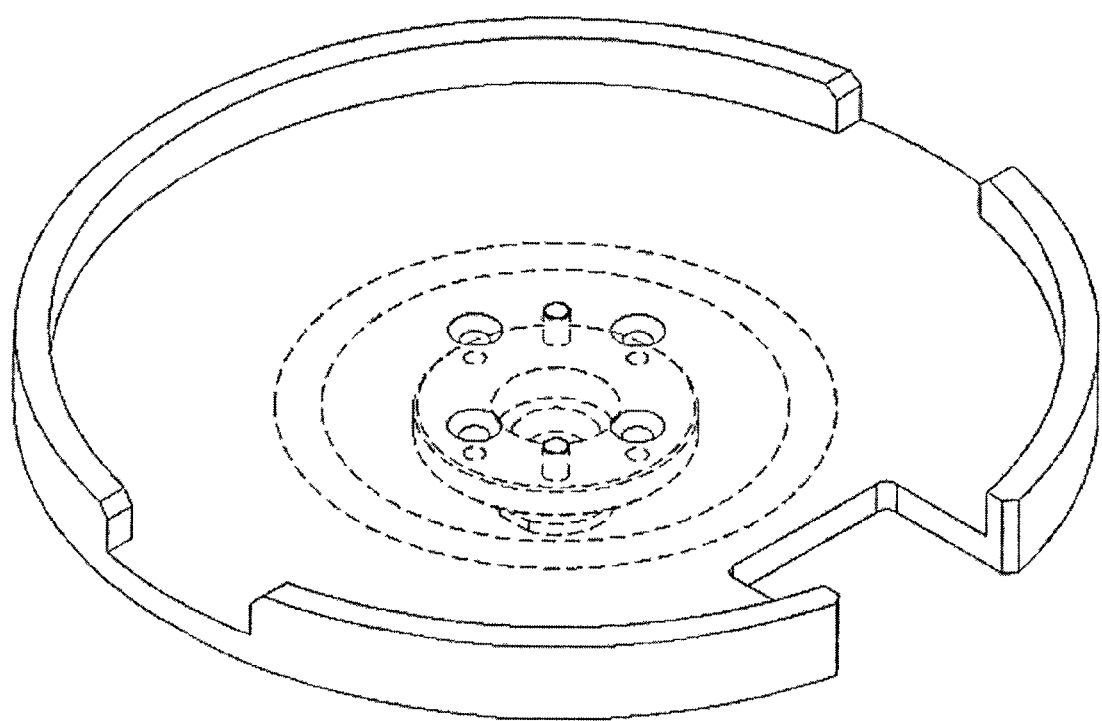
FIG. 15 is a perspective view of a driving part provided at the rotation driving device shown in FIG. 13.

FIG. 12 is a perspective view of the rotation driving device (120), FIG. 13 is a front view of the rotation driving device (120), FIG. 14 is a perspective view of a rotational part (129) provided at the rotation driving device (120), and FIG. 15 is a perspective view of a driving part (121) provided at the rotation driving device (120).

Referring to FIGS. 12-13, the rotation driving device (120) includes a motor (119) which is operated by electric power supplied from an outside, a rotational part (129) which is rotated by the motor (119), and a driving part (121) which is disposed at an upper side of the rotational part (129) so that only an inclination thereof is changed to be corresponding to a rotational direction of the rotational part (129) in a stopped state when the rotational part (129) is rotated.

Instead of the motor (119) supplied with electric power, other power supplying unit such as an electromotor or a generator can be used.

In FIG. 14, the rotational part 129 includes a rotational shaft (128) of which one end is coupled to the motor (119) to be rotated by the motor (119), a circular plate type first supporting part (126) which is disposed at a lower end of the rotational shaft (128) to rotatably support the rotational shaft (128), a first supporting part fixing portion (127) which is provided at a lower side of the first supporting part (126) to fix the first supporting part (126) to the rotational shaft (128), a circular plate type second supporting part (124) which is disposed at an upper side of the first supporting part (126) to be connected with the first supporting part (126) through a plurality of hinge members (125) and which is formed with an opening at a center portion thereof, a ball bearing receiving part (122) which is provided on circumference of an upper surface of the second supporting part (124) and formed with a spherical recessed portion to receive a part of the ball bearing, and a ball bearing (123) which is rotatably operated in the ball bearing receiving part (122).

The rotational part (129) is rotated by the motor (119), and the driving part (121) is operated to be corresponding to the rotational part (129), but maintained in the stopped state regardless of the rotation of the rotational part (129). The rotational shaft (128) fixed to the motor (119) is formed into a rod shape that its body (36) has a circular section. The rod can have a square section, a triangular section and the like, if it can be fixed to the motor (119).

It is apprehended that the end may be worn away due to its rotation or a component may be damaged where the end of the rotational shaft (128) contacted with the driving part (121) has an angular shape. Therefore, it is preferable that the rotational shaft (128) has a spherical end.

The first supporting part (126) is disposed at the lower end of the rotational shaft (128) fixed to the motor (119) to allow the rotational shaft (128) to be rotatably supported, and the rotational shaft (128) passes through a center portion of the first supporting part (126). Preferably, the first supporting part (126) is formed into a circular plate to maintain a stably balanced state upon the rotation thereof, but may have other types.

The first supporting part fixing portion (127) is provided at a lower side of the first supporting part (126) to function to fix the first supporting part (126) to the rotational shaft (128). In other words, where the rotational shaft (128) is rotated while only the first supporting part (126) is coupled to the rotational shaft (128), there is the possibility that the first supporting part (126) is separated from the rotational shaft (128) by gravity or centrifugal force. Therefore, the first supporting part fixing portion (127) functions to support the first supporting part (126).

In addition, the first supporting part fixing portion (127) functions to support a load of the first supporting part (126). Therefore, the first supporting part fixing portion (127) is formed of a rubber or other elastic member.

The second supporting part (124) is disposed at the upper side of the first supporting part (126), and the hinge member (125) is interposed between the first supporting part (126) and the second supporting part (124) to support the second supporting part (124).

The hinge member (125) is disposed in which a central axis thereof is positioned at a center portion of both contacting portions. Therefore, unlike a general hinge member of which a central axis exists at one side thereof and thus which can be pivoted only in one direction, the hinge member (125) of the present invention can be freely pivoted in a clockwise or counterclockwise direction.

A center portion of the second supporting part (124) is formed with an opening, and the spherical end of the rotational shaft (128) is protruded upward through the opening to be engaged with the power transmitting part (121).

The cylindrical ball bearing receiving part (122) with the spherical recessed portion is formed on circumference of the upper surface of the second supporting part (124) to receive a part of the ball bearing (123).

The ball bearing (123) is inserted into the recessed portion of the ball bearing receiving part (122) to be rolled. Since a large quantity of frictional heat is generated due to friction between the ball bearing receiving part (122) and the ball bearing (123), it is preferable that the ball bearing receiving part (123) is formed of a heat-resisting material.

Preferably, the ball bearing receiving part (122) and the ball bearing (123) inserted into it are formed at least three places to prevent the driving part (121) interlocked with the ball bearing (123) from being out of balance. In case there are provided three ball bearing receiving parts (122), the ball bearing receiving parts (122) are disposed to be spaced apart from each other at an angle of 120°, resulting that the driving part (121) is operated in a balanced mode.

The second supporting part (30) of the rotation driving device (100) shown in FIGS. 3-4 is provided with four ball bearings (45) and four ball bearing receiving parts (40). The ball bearing receiving parts (40) are disposed to be spaced apart from each other at an angle of 90°, so that the driving part (80) is operated in a balanced mode.

Referring to FIG. 15 showing the rotation driving device (120), the driving part (121) of the rotation driving device (120) has a circular plate shape for mounting the cell culture apparatus (100), and a member with a spherical recessed portion in which the spherical end of the rotational shaft (128) of the rotational part (129) is pivotably inserted is provided at the internal surface of the circular plate in a form of the sphere.

The ball bearing (123) of the rotational part (129) is directly contacted with the lower surface of the driving part (121) of the rotation driving device (120). A ball bearing passage (123) with an appropriate width is formed along a circumference of the lower surface of the driving part (121) to smoothly roll the ball bearing (123).

Referring to FIGS. 12-15, the operational principle of the rotation driving device (120) will be described as follows:

In the motor (119) operated, the rotational shaft (128) fixed to the motor (119) is rotated. Thus, the first second supporting part (126) and the first supporting part fixing portion (127) fixed to the rotational shaft (128) are rotated according to the rotation of the rotational shaft (128), and the second supporting part (124) is also rotated because it is connected with the first supporting part (126) through the hinge member (125).

When the rotational part (129) is rotated as a whole, the ball bearing (123) disposed at the upper surface of the second supporting part (124) is rolled in a reverse direction to a rotational direction of the rotational part (129). This is caused by friction force generated between a contacted surface of the ball bearing receiving part (122) of the ball bearing (123) and a contacted surface of the driving part (121) of the ball bearing (123).

Since the ball bearing (123) is rolled in a reverse direction to a rotational direction of the rotational part (129), the driving part (121) contacted with the ball bearing (123) is not rotated but maintained in a stopped state. The spherical end of the rotational shaft (128) is engaged with the member of the driving part (121), which has the spherical recessed portion, but since it does not exert an influence on the movement of the driving part (121) due to the rolling of the ball bearing (123), the driving part (121) is also maintained in the stopped state.

The second supporting part (124) and the cell culture device receiving part (100) interlocked with the second supporting part (124) are also inclined where the hinge member (125) is inclined to one side on its central axis for the rotation of the rotational shaft.

In the rotational part (129) rotated in a state inclined to one side, since the driving part (121) is maintained in the stopped state, it is periodically moved while only an inclination thereof is changed in the rotational direction of the rotational part (129).

In other words, as the driving part (121) is inclined in an inclined direction of the hinge member (125) of the rotational part (129) and the inclined direction is changed due to the rotation of the rotational part (129), an inclined direction of the driving part (121) is also changed. However, the driving part (121) is not rotated due to the rotation of the ball bearing (123).

Due to repeat of such motion as described above, the cells cultured in the cell culture apparatus (10) provided on the upper surface of the driving part (121) can be appropriately mixed, and the culture solution is equally distributed, whereby the cells in the cell culture apparatus are evenly grown.

In other words, since a part of the cells in the cell culture apparatus (100) is submerged under the culture solution and other part is exposed to an internal space of the cell culture apparatus (100) due to the rotation of the driving part (121), the consumption of the culture solution is reduced compared with a conventional flask culture in which the entire surface is submerged under the culture solution. Since oxygen is sufficiently supplied due to the rotation, the stability to glucose metabolism of the cells is increased compared with a conventional culture method.

In addition, it is convenient since it is not necessary for the user to shake the cell culture device in a manual manner. And since a large friction force is not generated therein, it can be used for a long time period without any damage.

Furthermore, according to the present invention, it is possible to control a rotational speed of the rotational part by providing a separate automatic control unit.

Figure 16:
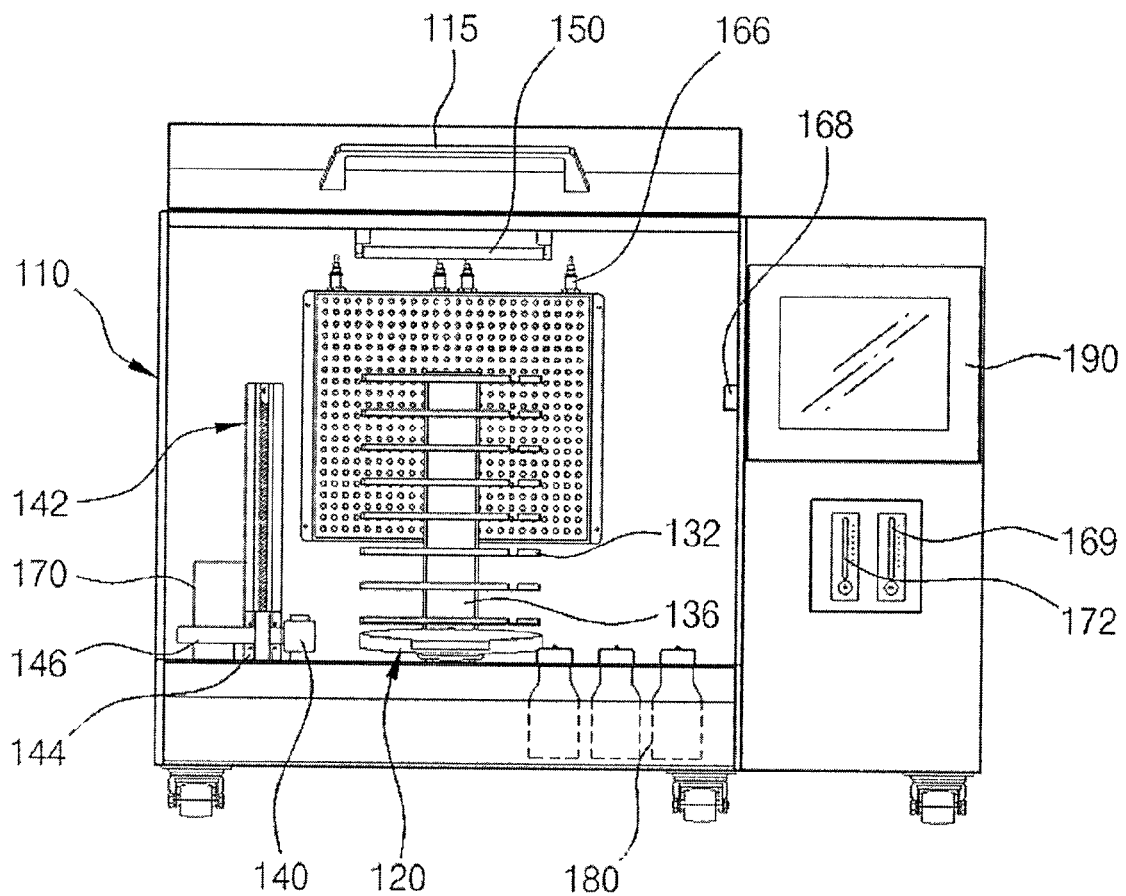
FIG. 16 is a front view of the mass automatic cell culture device in which the cell culture apparatus is not installed.
Figure 17:
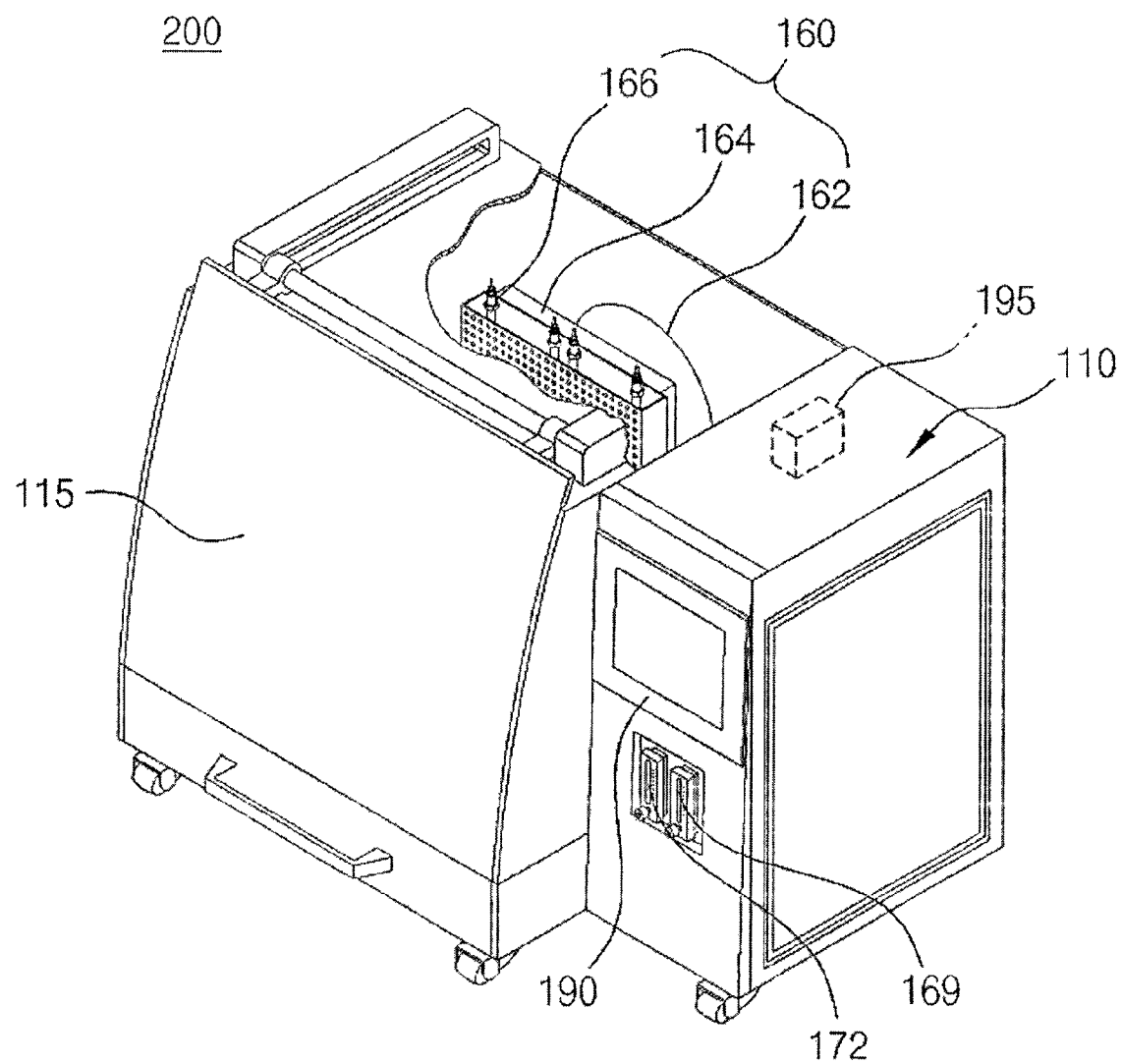
FIG. 17 is a view of a temperature controlling part of the mass automatic cell culture device.

FIG. 16 is a front view of the mass automatic cell culture device (200) in which the cell culture apparatus 100 is not installed, and FIG. 17 is a view of a temperature controlling part (160) of the mass automatic cell culture device (200).

As shown in FIG. 16 in which the cell culture apparatus (100) is not installed on the driving part (121) of the rotation driving device (120), there are provided the push unit (130), the observation unit (140) disposed at one side of the rotation driving device (120), the temperature controlling part (160) for controlling an internal temperature of the main body (110), the gas supplying part (170) which supplies gas to the cell culture apparatus (100), the ultraviolet radiating unit (150) which supplies ultraviolet light, and the culture storing part (180) which temporarily stores the collected culture solution in mass automatic cell culture device (200).

The vertical frame (142) is provided at one side of the rotation driving device (120), and the second robot arm (146) is disposed at a conveying member (144) which is vertically reciprocated on the vertical frame (142). The observation unit (140) is disposed at the end of the second robot arm (146) to be directed to the rotation driving part (120). In the conveying member (144) moved on the vertical frame (142) vertically, the second robot arm (146) is operated to be moved left and right. Therefore, the observation unit (140) disposed at the end of the second robot arm (146) is conveyed to a place where a user wants to observe. As results, the observation unit (140) is moved vertically and horizontally, generating that it is freely operated in a two-dimensional manner.

A CCD camera of which magnification is controlled could be used as the observation unit (140). According to the cell culture apparatus (100) installed, a user can easily observe the cells grown in the cell culture flask (10) from an outside by using the CCD camera.

Likewise, it is possible to store an image representing an amount of the observed cells and a culture state by setting a storing program.

The gas supplying part (170) is provided at a lower surface or a side surface in the main body to supply gas into the cell culture flask (10) of the cell culture apparatus (100). Therefore, it is possible to constantly supply various gases. A gas meter (172) for displaying an amount of supplied gas is provided at a front surface of the main body (110), and the amount of gas is externally shown using a liquid crystal display (190).

The ultraviolet radiating unit (150) is provided on the internal upper surface of the main body (110) to supply the ultraviolet light. The ultraviolet radiating unit (150) emits a blue ultraviolet light to sterilize the internal portion of the main body (110).

The culture storing part (180) is provided at the internal lower surface of the main body (110) in a bottle shape and The culture storing part (180) connected through the tube (182) to the injection unit (50) or the collection unit (60) permits to temporarily store the culture solution. The culture storing part (180) is provided in plural according to the necessity.

As represented in FIGS. 16-17, the temperature controlling part (160) is provided at a rear surface of the mass automatic cell culture device (200) to control the internal temperature of the main body (110).

The temperature controlling part (160) includes a fan (162) which is provided at one side of the main body (110) to supply an external air into the main body (110), a HEPA filter (164) which is disposed to be adjacent to the fan (162) at an internal surface of the main body (110) and purifies the external air supplied from the fan, a heat pipe which is disposed to be adjacent to the HEPA filter and supplies heat to the external air purified by the HEPA filter, a temperature sensor which is disposed at one side of the main body to measure an internal temperature of the main body (110), and a control part (195) which operates the fan (162) and the heat pipe where the temperature received from the temperature sensor (168) is lower than the preset temperature.

By providing the HEPA filter (164), it is not necessary to provide a separate air purifying unit, and it is possible to maintain the internal portion of the main body (110) in a cleaned state.

The heat pipe (166) is arranged to be bent, thereby supplying a large quantity of heat and thus increasing heat efficiency.

The temperature measured by the temperature sensor (168) is displayed on a temperature displaying part (169). Alternatively, the temperature measured is displayed by using the liquid crystal display 190.

The control part (195) can control an amount of the gas supplied to the cell culture apparatus (100), and also control the injection unit (50) and the collection unit (60) of the cell culture apparatus (100) to supply or discharge the culture solution.

Figure 18:
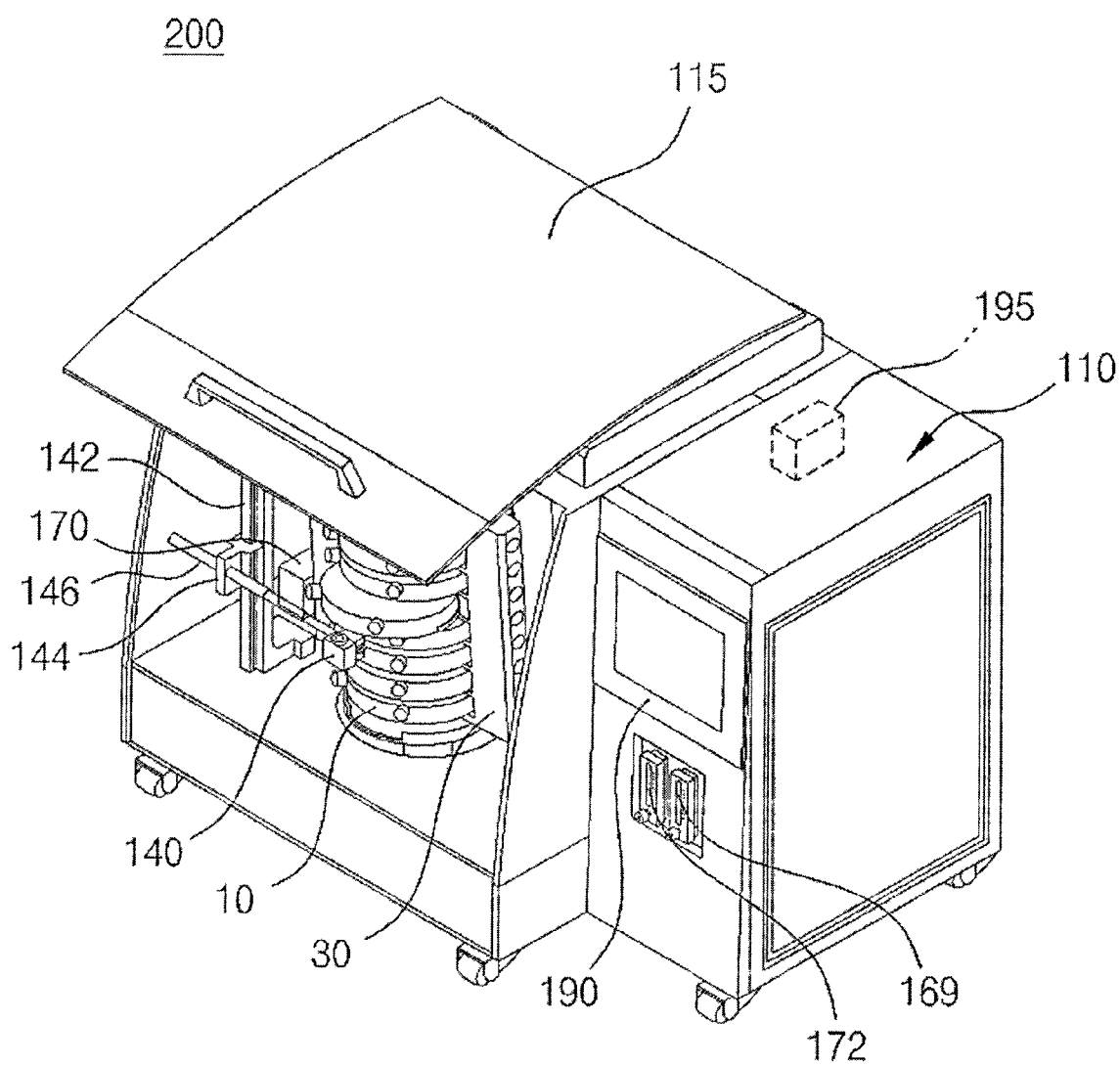
FIG. 18 is a view showing a status that the mass automatic cell culture device is operated.

FIG. 18 is a view showing a status that the mass automatic cell culture device 200 is operated. When a user operates the mass automatic cell culture device 200, the inclination of the cell culture apparatus (100) is changed along a circumference thereof by the rotation of the rotational driving device (120).

When the user wants to observe the internal portion of the cell culture flask (10) provided in the cell culture apparatus (100), the observation unit (140) can be moved near the cell culture flask (10) to be observed by the two-dimensional movement of the vertical frame (142) and the second robot arm (146). Then, the user can observe the cells in the cell culture flask (10) through the observation unit (140) and thus determine a growth level of the cells and whether the culture solution is insufficient.

By setting a program in the mass automatic cell culture device (200), it is possible to automatically control the rotation of the rotation driving device (120), the supply and discharge of the culture solution, the internal temperature of the cell culture device (200), and the supply of the gas.

Figure 19:
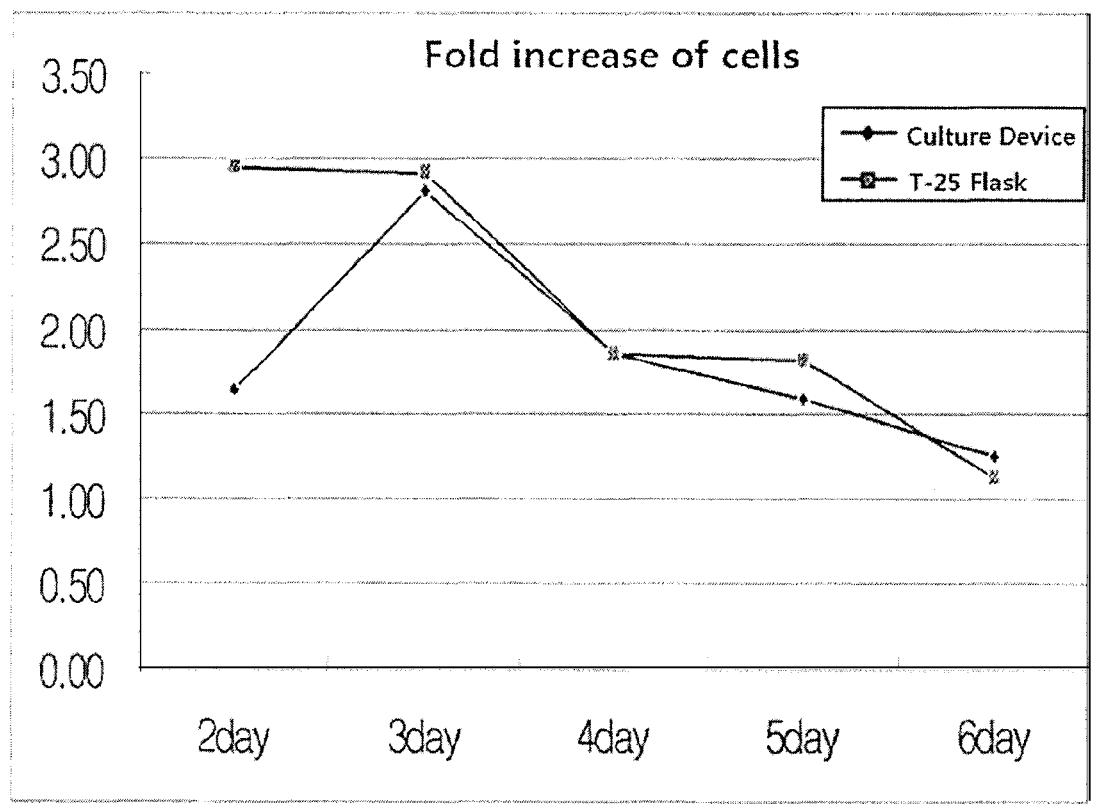
FIG. 19 is a view showing an fold increase of articular cartilage cell in the present mass automatic cell culture device and a general flask.
Figure 20:
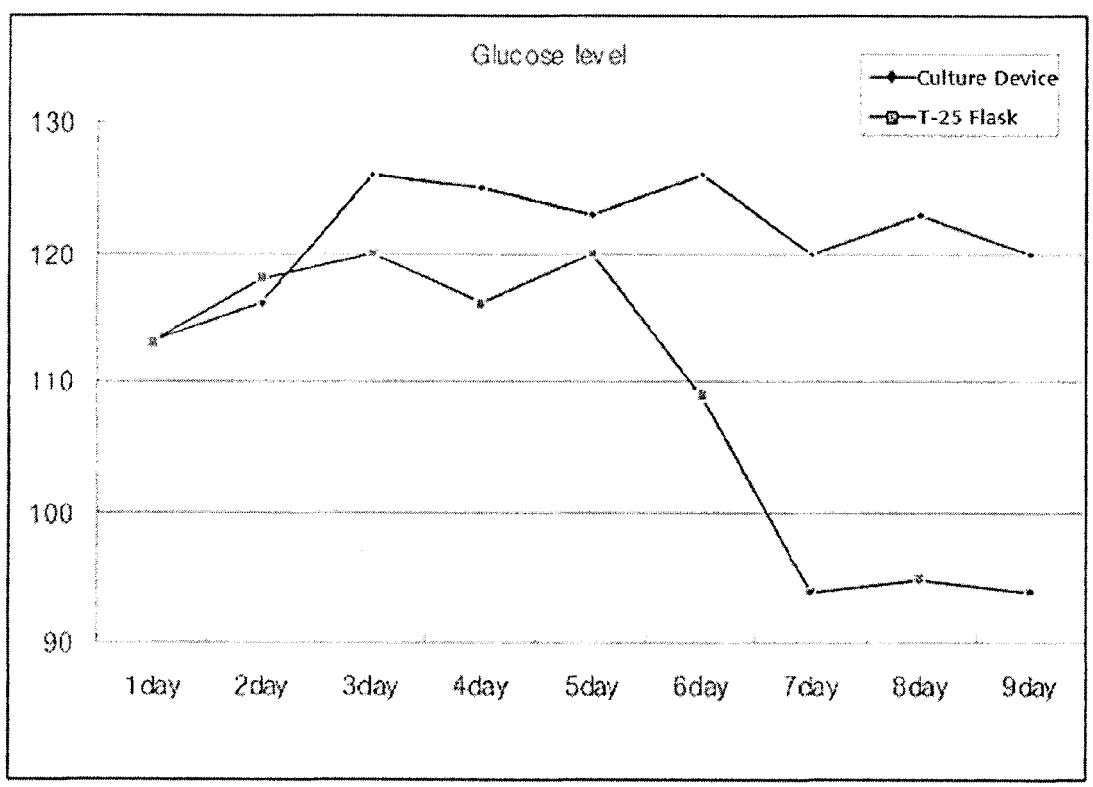
FIG. 20 is view showing a glucose level measured every day in the present mass automatic cell culture device and the general flask.

FIG. 19 is a view showing an increased multiple of articular cartilage cell in each case of using the mass automatic cell culture device 200 and a general flask, and FIG. 20 is view showing a glucose level measured everyday in each case of using the mass automatic cell culture device 200 and the general flask.

FIG. 19 is a view showing a fold increase of articular cartilage cells in the present mass automatic cell culture device (200) and a general flask, and FIG. 20 is view showing a glucose level measured every day in the present mass automatic cell culture device (200) and the general flask.

The articular cartilage cells (AC cells) were cultured by using the present mass automatic cell culture device (200). After freeze-preserved AC cells from 8th passage are defrosted, the AC cells were seeded in the cell culture apparatus (100) at a low density of 850 cells/cm$^2$ and then cultured for 9 days without exchange of the culture medium.

During the cell culture, the conditions in the cell culture apparatus (100) were maintained as follows: 6.5% of $CO_2$ concentration, 37° C. at temperature, and 1 rpm with a rotational speed of the cell culture flask (10). As a comparative example, the same AC cells were seeded in a general flask (T-25 flask) at the same density and then stationary cultured in a $CO_2$ incubator under the same culture conditions ($CO_2$ of 6.5%, temperature of 37° C.).

During the culture of seeded AC cells, the number of cells was measured every day to calculate a fold increase, and a glucose level was also measured every day by using a glucometer. As results, the fold increase of the cells is similar in the two examples, but the glucose level is higher in the cell culture apparatus (100) of the present invention compared with the T-25 flask. In other words, since oxygen is sufficiently supplied in the cell culture apparatus (100) of the present invention by the rotation driving, the consumption of the glucose is reduced during the cell culture. Consequently, it could be appreciated that the cell culture in the present cell culture apparatus (100) has higher energy metabolism efficiency than the stationary culture in the general flask (T-25).

The glucose is an energy source for the cells, which is commonly contained in the culture medium. Where the oxygen supply is sufficient, the glucose is metabolized through glycolysis into pyruvate in the body and then oxidized in the citric acid cycle to produce $CO_2$ and water. However, where the oxygen supply is insufficient, the pyruvate does not enter the citric acid cycle, but enters the lactate fermentation process for energy production. Furthermore, the glycolysis is repeated to metabolize the glucose, and the citric acid cycle is not normally operated, and lactic acid is accumulated.

The fact that the glucose level is reduced compared with the fold increase of the cells means that the citric acid cycle is not normally operated due to lack of oxygen. Ultimately, it means that the culture method of the present invention using the rotation driving is further advantageous in metabolizing the glucose compared with the stationary culture using the general flask (T-25).

According to the cell culture flask (10) of the present invention, since the cells can be adhered within a cylindrical culture tube, the culture space is maximized. The cells is alternatively contacted with the culture medium and air to sufficiently receive the air as a part of the cells adhered in the culture tube is submerged under the culture solution and other part is exposed to the internal space of the culture tube due to the rotation driving.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A cell culture apparatus, comprising:
   (a) a plurality of cylindrical cell culture flasks which are each: (i) air-tightly sealed to culture a cell using a culture solution and various gases, (ii) formed of a transparent material to permit observation of an internal portion thereof, (iii) formed into a cylindrical shape with a predetermined height, and (iv) comprise a culture space for cell culture;
   (b) a plurality of injection units for supplying the cell and the culture solution into the plurality of cell culture flasks;
   (c) a plurality of collection units for collecting the cell and the culture solution from the plurality of cell culture flasks; and
   (d) a cell culture flask receiving part which is comprised of (i) first and second vertical frames in which a plurality of injecting parts and a plurality of collecting parts for respectively receiving the plurality of injection units and the plurality of collection units are vertically formed to be opposed to each other, and (ii) plate-shaped connection parts for receiving the plurality of cell culture flasks, which are respectively disposed between upper ends and lower ends of the first and second vertical frames spaced apart from each other in regular intervals, thereby connecting the first and second vertical frames, wherein the plurality of injecting parts and the plurality of collecting parts are aligned along the first and second vertical frames, respectively, and individually provide a space for a reciprocating action of the plurality of injection units and the plurality of collection units, wherein the first vertical frame is connected with the second vertical frame through the plate-shaped connection parts,
   wherein at a side surface of each of the cell culture flasks is formed a culture solution inlet port for introducing the culture solution or the cell into the culture space, a culture solution outlet port for discharging the culture solution or the cell from the culture space, a gas inlet port and a gas outlet port to introduce and discharge the various gases into/from the culture space, and a foreign substance inlet port to introduce a foreign substance, wherein each of the culture solution inlet port and the culture solution outlet port protrude from an outer surface of each of the cell culture flasks and have a narrow end, wherein all ports are formed along a side surface of each of the cell culture flasks in order of the culture solution inlet port, the gas inlet port, the gas outlet port, the culture solution outlet port, and the foreign substance inlet port, wherein each of the cell culture flasks are directly connected to one of the plurality of the injection units and one of the plurality of the collection units through the culture solution inlet port and the culture solution outlet port;
   wherein the plurality of injection units and the plurality of collection units each comprise:
   (i) a syringe part with a power supply; (ii) a culture solution storing part which is connected with the syringe part, wherein the culture solution storing part is formed into a bottle shape for receiving the culture solution; (iii) a contact part which is connected with the culture solution storing part and is configured to flow the culture solution to each of the cell culture flasks, wherein the contact part is formed at an end of the syringe part and is funnel-shaped; (iv) a piston member which is disposed to be reciprocated inside the culture solution storing part; and (v) a connection member of which one end is connected with the piston member and the other end is connected with the power supply, wherein the connection member comprises a linear rod or a lead screw.

2. The cell culture apparatus according to claim 1, wherein the foreign substance inlet port is opened and closed by a cylindrical stopper.

3. The cell culture apparatus according to claim 1, wherein each of the cell culture flasks is formed of a transparent plastic or a non-fragile tempered glass.

4. The cell culture apparatus according to claim 1, wherein the collecting parts are formed of a transparent plastic or a stainless steel.

5. The cell culture apparatus as set forth in claim 1, wherein the power supply comprises a motor which is operated by electric power supplied through a cable from an outside.

* * * * *